(12) United States Patent
Guo

(10) Patent No.: US 10,959,747 B1
(45) Date of Patent: Mar. 30, 2021

(54) TISSUE REMOVING

(71) Applicant: Lifei Guo, Brookline, MA (US)

(72) Inventor: Lifei Guo, Brookline, MA (US)

(*) Notice: Subject to any disclaimer, the term of this patent is extended or adjusted under 35 U.S.C. 154(b) by 149 days.

(21) Appl. No.: 16/372,867

(22) Filed: Apr. 2, 2019

Related U.S. Application Data

(60) Provisional application No. 62/651,452, filed on Apr. 2, 2018.

(51) Int. Cl.
| | |
|---|---|
| *A61B 17/32* | (2006.01) |
| *A61B 17/3205* | (2006.01) |
| *A61B 90/98* | (2016.01) |
| *A61B 17/00* | (2006.01) |

(52) U.S. Cl.
CPC .......... *A61B 17/32* (2013.01); *A61B 17/3205* (2013.01); *A61B 90/98* (2016.02); *A61B 2017/008* (2013.01); *A61B 2017/00221* (2013.01); *A61B 2017/320052* (2013.01)

(58) Field of Classification Search
CPC ....... A61F 2/12; A61B 90/02; A61B 10/0041; A61B 2017/008; A61B 2017/00796; A61B 5/4312; A61B 34/30
USPC ........................................................ 606/167
See application file for complete search history.

(56) References Cited

U.S. PATENT DOCUMENTS

| | | | |
|---|---|---|---|
| 4,356,826 A | 11/1982 | Kubota | |
| 6,254,614 B1 | 7/2001 | Jesseph | |
| 6,558,407 B1 | 5/2003 | Ivanko et al. | |
| 7,440,793 B2 | 10/2008 | Chauhan et al. | |
| 8,109,940 B2 | 2/2012 | McGuckin, Jr. | |
| 8,821,573 B2 | 9/2014 | Khouri et al. | |
| 9,468,519 B2 | 10/2016 | Kronowitz | |
| 2004/0024433 A1 | 2/2004 | Roy et al. | |

(Continued)

FOREIGN PATENT DOCUMENTS

WO    2005089065 A2    9/2005

OTHER PUBLICATIONS

Rabin, Roni C., "Cancer Patients Are Getting Robotic Surgery. There's No Evidence It's Better.", The New York Times; https://www.nytimes.com/2019/03/11/health/robotic-surgery-cancer.html?action=click&module=Discovery&pgtype=Homepage Mar. 11, 2019, 4 Pages.

(Continued)

*Primary Examiner* — Katherine M Shi
*Assistant Examiner* — Alyssa M Keane
(74) *Attorney, Agent, or Firm* — Lifei Guo

(57) ABSTRACT

Devices, systems, and methods of the present disclosure are directed to efficient and accurate removal of tissue from a three-dimensional anatomic structure, such as a breast, of a patient. For example, a cup can be positioned on the patient's breast to conform the breast (e.g. via suction) to a known three-dimensional contour, and a cutting tip can be moved along the three-dimensional contour at one or more predetermined distances from at least one surface of the cup. The cutting tip can remove tissue along the three-dimensional contour to form a skin envelope. As compared to a manual process performed by a surgeon, formation of the envelope through controlled movement of the cutting tip along the three-dimensional contour can improve control over dimensions of the envelope, thus, facilitating achievement of consistent outcomes by reducing the likelihood of complications associated with an envelope that is too thick, too thin, or uneven.

8 Claims, 13 Drawing Sheets

(56) References Cited

U.S. PATENT DOCUMENTS

| | | |
|---|---|---|
| 2004/0049251 A1 | 3/2004 | Knowlton |
| 2004/0215101 A1 | 10/2004 | Rioux et al. |
| 2005/0267389 A1 | 12/2005 | Copelan |
| 2006/0020279 A1 | 1/2006 | Chauhan et al. |
| 2011/0118625 A1* | 5/2011 | Akuzawa ........... A61B 10/0233 600/567 |
| 2015/0088122 A1 | 3/2015 | Jensen |
| 2016/0106516 A1 | 4/2016 | Mesallum |
| 2016/0228143 A1 | 8/2016 | Pomahac et al. |
| 2016/0334864 A1 | 11/2016 | Cheatham, III et al. |
| 2017/0042608 A1 | 2/2017 | Clark, III et al. |
| 2018/0008359 A1 | 1/2018 | Randle |

OTHER PUBLICATIONS

U.S. Patent and Trademark Office, copending U.S. Appl. No. 16/372,924 Notice of Allowance dated Nov. 13, 2020, 17 pages.
U.S. Patent and Trademark Office, copending U.S. Appl. No. 16/372,802 Non-Final Office Action dated Nov. 5, 2020, 19 pages.

* cited by examiner

TISSUE REMOVING

CROSS-REFERENCE TO RELATED APPLICATIONS

This application claims the benefit of priority to U.S. Provisional Patent Application No. 62/651,452, filed Apr. 2, 2018, the entire contents of which are hereby incorporated herein by reference.

BACKGROUND

Breast cancer treatment often includes surgical intervention. For example, a lumpectomy can be performed to remove abnormal tissue, and a portion of surrounding tissue, from the breast while conserving as much breast tissue as possible. As another example, a mastectomy can be performed to remove all breast tissue from a breast of the patient, leaving a skin envelope. In many cases, following the mastectomy, breast implants can be placed in the skin envelope as part of a reconstructive surgery. Historically, a mastectomy can be part of the treatment of breast disease in instances in which a lumpectomy is not feasible although that trend is changing and mastectomy is increasingly becoming a first line of surgical treatment.

Although it is a more invasive option, a mastectomy is sometimes chosen as an alternative to the less invasive option of a lumpectomy. For example, some patients with early-stage disease treatable with a lumpectomy may, nevertheless, opt for a mastectomy for a variety of reasons, such as to avoid radiation treatment or to have more aesthetic reconstruction. As another example, some patients with no cancer diagnosis but with a genetic predisposition to breast cancer, may opt for a prophylactic mastectomy. Thus, in recent years, the number of mastectomies has increased, even as the diagnosis of breast cancer has been stable.

While mastectomies can be an effective part of breast cancer treatment or prevention, the surgery is performed manually and the anatomic geometry is three-dimensional and highly variable from patient to patient. Thus, mastectomies can be time consuming and subject to variable outcomes. More specifically, a mastectomy can take between about 60-120 minutes per breast to perform, depending on the size, shape, tissue quality of the breast, and the skill set of the mastectomy surgeon. Because of the complex nature of this manual procedure, the consistency and quality of a skin envelope formed through removal of the breast tissue can deviate from an ideal skin envelope. If the skin envelope is too thick, breast tissue may be left behind, increasing the risk of recurrence of the cancer. Conversely, if the skin is too thin, the skin envelope may suffer ischemia, resulting in wound healing problems, and in the case of reconstruction, potential loss of implants. Thus, there remains a need for reducing the time associated with performing a mastectomy while also reducing deviations from an ideal skin envelope.

SUMMARY

Devices, systems, and methods of the present disclosure are directed to efficient and accurate removal of tissue from a three-dimensional anatomic structure, such as a breast, of a patient. For example, a cup can be positioned on the patient's breast to conform the breast (e.g., via suction) to a known three-dimensional contour, and a cutting tip can be moved along the three-dimensional contour at one or more predetermined distances from at least one surface of the cup. The cutting tip can remove tissue along the three-dimensional contour to form a skin envelope. As compared to a manual process performed by a surgeon, formation of the envelope through controlled movement of the cutting tip along the three-dimensional contour can improve control over dimensions of the envelope, thus facilitating achievement of consistent outcomes by reducing the likelihood of complications associated with an envelope that is too thick, too thin, or uneven.

According to one aspect, a system for removal of tissue from a patient can include a cup and a cutting head. The cup can have at least one surface, the at least one surface defining a volume and a first opening, and the volume positionable about a breast of a patient with the at least one surface of the cup facing a skin surface of the breast and the first opening circumscribing the breast of the patient. The cutting head can be secured (e.g., releasably secured) to the cup, and the cutting head can include an actuator and a cutting tip. The actuator can be coupled to the cutting tip, and the actuator can be controllable to move the cutting tip, within the volume, along a three-dimensional contour at one or more predetermined distances from the at least one surface defining the volume and the first opening.

In certain implementations, the actuator can be controllable to move the cutting tip along the three-dimensional contour parallel to the at least one surface of the cup. Further, or instead, one or more of the volume and the first opening can be symmetric about at least one plane perpendicular to the first opening.

In certain implementations, a cross-section of the volume in at least one plane parallel to the first opening is curvilinear. For example, the cross-section of the volume in the at least one plane parallel to the first opening can be substantially elliptical. Further, or instead, the volume defined by the at least one surface of the cup can be frustoconical. Additionally, or alternatively, at least one portion of the volume can be concave. That is, for example, at least one portion of the volume can have a two-dimensional curvilinear profile (e.g., an arc) in one or more planes perpendicular to the first opening.

In some implementations, the at least one surface of the cup can further define a second opening, the volume extending from the first opening to the second opening, and the cutting head extending through the second opening. The volume can be, for example, symmetric about at least one plane intersecting the first opening and the second opening. Further, or instead, the first opening can have a first area and the second opening can have a second area, and the second area can be less than the first area. In certain instances, a gasket can be disposed along the first opening. The gasket can be pliable (e.g., formed of one or more of silicone or rubber) The gasket can be, for example, releasably positionable along the first opening.

In certain implementations, the actuator can include a pivot arm and an extension arm coupled to the pivot arm. The pivot arm and the extension arm can be movable in coordination with one another to move the cutting tip along the three-dimensional contour. In certain instances, the pivot arm can be rotatable about a first axis defined by the pivot arm, the extension arm can be axially movable along a second axis defined by the extension arm and intersecting the first axis, and the pivot arm and the extension arm can be movable relative to one another to change an included angle between the first axis and the second axis.

In some implementations, the cutting tip can include a resistance element. For example, the cutting tip can define a track, and the resistance element can be movable back and forth along the track. The cutting tip can include, for example, one or more sensors adjacent to the resistance element. The one or more sensors can include tissue sensors. Returning to the example of the resistance element movable alone a track, at least one of the tissue sensors can be disposed on each side of the track along which the resistance element is movable. Further, or instead, the one or more sensors can include a pressure sensor arranged to detect contact pressure between the cutting tip and tissue. Additionally, or alternatively, the one or more sensors can include a capacitance sensor. Still further or instead, the one or more sensors can include a blood sensor, a temperature sensor, or both. In some instances, the cutting tip can include a position sensor configured to sense a distance from the cutting tip to the at least one surface of the cup defining the volume and the first opening. In certain instances, the cutting tip can define one or more suction channels adjacent to the resistance element.

In some implementations, at least one of the cutting head and the cup can define a suction lumen in fluid communication with the volume defined by the at least one surface of the cup. In some instances, the system can further include a suction source in fluid communication, via the suction lumen, with the volume defined by the at least one surface of the cup, wherein, with the cup positioned about the breast of the patient, the suction source is actuatable to form vacuum pressure in the volume to draw the skin surface of the breast toward the at least one surface of the cup.

In certain implementations, the at least one surface of the cup can be rigid upon exposure to vacuum pressure.

In some implementations, the system can further include an adhesive disposed along at least a portion of the at least one surface of the cup.

In certain implementations, at least a portion of the at least one surface of the cup can be textured to resist movement of the at least one surface of the cup relative to the skin surface of the patient.

In some implementations, the system can further include a controller in electrical communication with the actuator and the cutting tip, the controller including one or more processors and a non-transitory, computer readable storage medium having stored thereon computer executable instructions for causing the one or more processors to send one or more control signals to the actuator, the one or more control signals associated with positioning the cutting tip along the three-dimensional contour at the one or more predetermined distances from the at least one surface defining the volume and the first opening, and send an activation signal to the cutting tip to dissect tissue along the three-dimensional contour. Further or instead, the non-transitory, computer readable storage medium can have further stored thereon computer executable instructions for causing the one or more processors to receive an electrical signal indicative of size of the cup and, based on a size of the cup, determine the three-dimensional contour. In certain instances, the cup can include, for example, a transmitter including size information related to the cup, the cutting head includes a receiver configured to communicate with the transmitter to receive a signal indicative of the size information related to the cup. Further, or instead, the transmitter can include a passive electrical circuit, the passive electrical circuit having one or more electrical characteristics indicative of the size information related to the cup. Still further or instead, the transmitter can be configured for wireless communication with the receiver. Additionally, or alternatively, the transmitter can be connectable in wired electrical communication with the receiver. In certain instances, the cutting tip can define a tip axis and the one or more control signals can control an angle of the tip axis tangent to the three-dimensional contour. Still further or instead, the non-transitory, computer readable storage medium can have further stored thereon computer executable instructions for causing the one or more processors to receive at least one user input corresponding to the one or more predetermined distances from the at least one surface defining the volume and the first opening.

According to another aspect, a device can include a cup, a coupling, and a transmitter. The cup can define a first opening and a second opening, the cup having at least one surface extending from the first opening to the second opening, the at least one surface defining a volume positionable about a breast of a patient with the at least one surface of the cup facing a skin surface of the breast and the first opening circumscribing the breast of the patient. The coupling can be disposed on the cup and adjacent to the second opening, the coupling releasably securable in sealed engagement with a cutting head extending through the second opening. The transmitter can be carried on the cup, the transmitter including information related to the cup.

In some implementations, a cross-section of the volume in at least one plane parallel to the first opening can be curvilinear. For example, the cross-section of the volume in the at least one plane parallel to the first opening is substantially elliptical. In some instances, the volume defined by the at least one surface of the cup can be frustoconical. Further, or instead, at least one portion of the volume can be concave. As an example, at least a portion of the volume has a two-dimensional curvilinear profile (e.g., an arc) in one or more planes perpendicular to the first opening.

In certain implementations, a cross-section of the volume can be symmetric about at least one plane intersecting the first opening and the second opening. For example, at least one plane bisects the first opening and the second opening.

In some implementations, the at least one surface of the cup can be rigid upon exposure to vacuum pressure.

In certain implementations, the device can further include a gasket (e.g., a pliable gasket) disposed about the second opening. The gasket can be releasably positionable along the second opening. Additionally, or alternatively, the gasket can be formed of silicone, rubber, or a combination thereof.

In some implementations, the device can further include an adhesive disposed on at least a portion of the at least one surface along the volume.

In certain implementations, the transmitter can be activatable to transmit the information related to the cup to a remote receiver. The transmitter can include, for example, a passive RFID tag.

In some implementations, the transmitter can include a portion of an electrical circuit, the portion of the electric circuit having one or more electrical properties indicative of the information related to the cup, the transmitter connectable in electrical communication with a receiver carried on the cutting head to complete the electrical circuit. The portion of the electric circuit can have, for example, a predetermined impedance associated with size information of the cup. Further, or instead, the transmitter can include one or more conductive pins, the one or more conductive pins associated with size information of the cup, and the one or more conductive pins connectable with respective one or more receptacles defined by the receiver carried on the cutting head to complete the electrical circuit.

In certain implementations, the transmitter can include a memory, the memory having stored thereon information related to use history of the cup.

In some implementations, the transmitter can be connectable in optical communication with a receiver carried on the cutting head. For example, the transmitter can include a QR code, a bar code, or both associated with size of the cup. Additionally, or alternatively, the transmitter can be activatable to transmit light of a predetermined wavelength associated with size of the cup.

According to yet another aspect, a method of controlling three-dimensional dissection of tissue can include receiving an identification signal indicative of size of a cup, the cup having at least one surface, the at least one surface defining a volume and a first opening, based on the identification signal, determining a three-dimensional contour within the volume, the three-dimensional contour spaced apart from the at least one surface at one or more predetermined distances, sending one or more control signals to an actuator coupled to a cutting tip, the actuator coupled to the cup and extending into the volume defined by the at least one surface of the cup, the one or more control signals associated with positioning the cutting tip along the three-dimensional contour, and sending an activation signal to the cutting tip to dissect tissue along the three-dimensional contour to form at least a portion of a skin envelope.

In certain implementations, receiving the identification signal can include sending an interrogation signal to the cup. The interrogation signal can be, for example, an electrical signal. Further, or instead, the interrogation signal can be an optical signal. Still further, or instead, the interrogation signal can be an RF signal.

In some implementations, the identification signal can be further indicative of use history of the cup, and sending the one or more control signals to the actuator can be based on whether the use history of the cup is below a predetermined threshold.

In certain implementations, the three-dimensional contour can be parallel to and spaced apart from the at least one surface of the cup.

In some implementations, determining the three-dimensional contour within the volume can include receiving the one or more predetermined distances from an input device.

In certain implementations, determining the three-dimensional contour within the volume can include detecting one or more electrical properties of the identification signal, the one or more electrical properties associated with a size of the cup. Further, or instead, the one or more electrical properties of the identification signal can include detecting a predetermined impedance associated with the size of the cup. Additionally, or alternatively, the one or more electrical properties of the identification signal can include detecting a pin configuration of the cup, the pin configuration associated with the size of the cup.

In some implementations, determining the three-dimensional contour within the volume can include detecting one or more optical properties of the identification signal, the one or more optical properties associated with the size of the cup. For example, the one or more optical properties can include a predetermined wavelength of light associated with size of the cup.

In certain implementations, the actuator can have a plurality of degrees of freedom, and sending the one or more control signals to the actuator can include sending a respective control signal associated with each degree of freedom of the actuator.

In some implementations, the cutting tip can define a tip axis, and the one or more control signals can position the tip axis tangent to the three-dimensional contour.

In certain implementations, the method can further include sending an alert signal to a user interface, the alert signal based on proximity of the cutting tip to a predetermined region of the volume.

According to still another aspect, a computer program product is encoded on one or more non-transitory computer storage media, the computer program product comprising instructions that, when executed by one or more computing devices, cause the one or more computing devices to perform operations including receiving an identification signal indicative of size of a cup, the cup having at least one surface, the at least one surface defining a volume and a first opening, based on the identification signal, determining a three-dimensional contour within the volume, the three-dimensional contour spaced apart from the at least one surface at one or more predetermined distances, sending one or more control signals to an actuator coupled to a cutting tip, the actuator coupled to the cup and extending into the volume defined by the at least one surface of the cup, the one or more control signals associated with positioning the cutting tip along the three-dimensional contour, and sending an activation signal to the cutting tip to dissect tissue along the three-dimensional contour to form at least a portion of a skin envelope.

According to yet another aspect, a computer program product is encoded on one or more non-transitory computer storage media, the computer program product comprising instructions that, when executed by one or more computing devices, cause the one or more computing devices to perform operations including receiving a signal indicative of a vacuum pressure in a volume at least partially defined by at least one surface of a cup, positioning a cutting tip along a three-dimensional contour within the volume, the three-dimensional contour spaced apart from the at least one surface of the cup at one or more predetermined distances, and, based on the received signal, selectively activating the cutting tip to dissect tissue of a patient along the three-dimensional contour.

In certain implementations, the signal indicative of the vacuum pressure in the volume can be received from a pressure sensor in fluid communication with the volume.

In some implementations, the signal indicative of the vacuum pressure in the volume can be received over a predetermined period of time. For example, selectively activating the cutting tip to dissect tissue of the patient along the three-dimensional contour can be at least partially based on a fluctuation of the received signal over the predetermined period of time.

In certain implementations, positioning the cutting tip along the three-dimensional contour within the volume can include sending one or more control signals to an actuator mechanically coupled to the cup and to the cutting tip. The actuator can have a plurality of degrees of freedom, and sending the one or more control signals to the actuator can include sending a respective control signal associated with each degree of freedom of the actuator. Further, or instead, the cutting tip can define a tip axis, and the one or more control signals can position the tip axis tangent to the three-dimensional contour.

In some implementations, the three-dimensional contour can be at least a portion of an ellipsoid.

In some implementations, selectively activating the cutting tip can include delivering energy to the cutting tip based on whether the received signal corresponds to a condition at or below a predetermined vacuum pressure in the volume.

In certain implementations, the computer program product can further include instructions that, when executed by one or more computing devices, cause the one or more computing devices to perform operations further including repeating the steps of receiving the signal, positioning the cutting tip along the three-dimensional contour within the volume, and selectively activating the cutting tip to dissect tissue to form a skin envelope.

According to still another aspect, a method can include receiving a signal indicative of a vacuum pressure in a volume at least partially defined by at least one surface of a cup disposed about a breast of a patient with the breast of the patient extending into the volume, positioning a cutting tip along a three-dimensional contour within the volume, the three-dimensional contour spaced apart from the at least one surface of the cup at one or more predetermined distances, and, based on the received signal, selectively activating the cutting tip to dissect tissue of a patient along the three-dimensional contour.

In certain implementations, the signal indicative of the vacuum pressure can be received from a pressure sensor in fluid communication with the volume.

In some implementations, the signal indicative of the vacuum pressure in the volume can be received over a predetermined period of time. For example, selectively activating the cutting tip to dissect tissue of the patient along the three-dimensional contour can be at least partially based on a fluctuation of the received signal over the predetermined period of time.

In some implementations, positioning the cutting tip along the three-dimensional contour within the volume can include sending one or more control signals to an actuator mechanically coupled to the cup and to the cutting tip. For example, the actuator can have a plurality of degrees of freedom, and sending the one or more control signals to the actuator can include sending a respective control signal associated with each degree of freedom of the actuator. Further, or instead, the cutting tip can define a tip axis, and the one or more control signals can position the tip axis tangent to the three-dimensional contour.

In certain implementations, selectively activating the cutting tip can include delivering energy to the cutting tip based on whether the received signal corresponds to a condition at or below a predetermined vacuum pressure in the volume.

According to still another aspect, a method of removing breast tissue from a patient can include selecting a cup, the cup having one or more surfaces, the one or more surfaces defining a volume and a first opening, securing the cup to a cutting head including an actuator and a cutting tip, the actuator controllable to move the cutting tip, making an incision in a breast of the patient, and positioning the cup about the breast of the patient with the one or more surfaces of the cup facing a skin surface of the breast and the first opening circumscribing the breast of the patient, wherein, with the cup positioned about the breast of the patient, the cutting tip extends through the incision and into the breast.

In certain implementations, selecting the cup can include providing a verification input to a user interface in electrical communication with the cutting head.

In some implementations, the cup can be selected from a plurality of cups, the plurality of cups spanning a range of sizes, and the cup is selected based on a size of the breast.

In certain implementations, making the incision can include removing an areola complex of the breast.

In some implementations, positioning the cup about the breast of the patient can include substantially centering the cup relative to the incision in the breast of the patient.

In certain implementations, positioning the cup about the breast of the patient can include anchoring the skin surface of the breast in a fixed position relative to the one or more surfaces of the cup facing the skin surface of the breast. For example, anchoring the skin surface of the breast in the fixed position relative to the one or more surfaces of the cup facing the skin surface of the breast can include creating vacuum pressure between the skin surface of the breast and the one or more surfaces of the cup facing the skin surface of the breast.

In certain implementations, positioning the cup about the breast of the patient can include placing a gasket along the first opening defined by the one or more surfaces of the cup.

In some implementations, the method can further include operating the cutting head, wherein activating the cutting head can include delivering energy to the cutting tip to dissect tissue and actuating the actuator to move the cutting tip along a three-dimensional contour at one or more predetermined distances from the one or more surfaces defining the volume and the first opening. As an example, activating the cutting head can include providing the one or more predetermined distances to a user interface in electrical communication with the cutting head. Further, or instead, activating the cutting head can further include providing suction adjacent to the cutting tip.

Other aspects, features, and advantages will be apparent from the description and drawings, and from the claims.

BRIEF DESCRIPTION OF THE DRAWINGS

Like reference symbols in the various drawings indicate like elements.

DESCRIPTION

Figure 1:
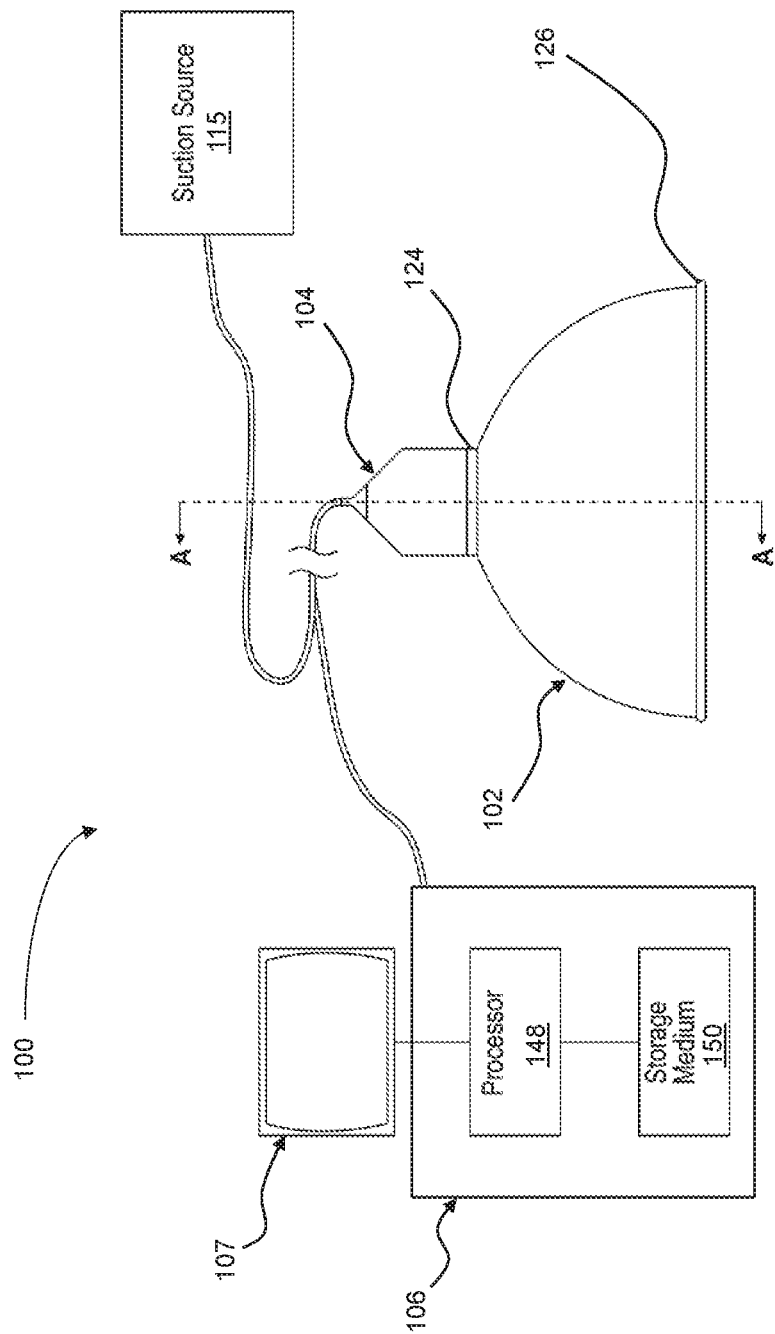
FIG. 1 is a front view of a system for removal of breast tissue.

Embodiments will now be described with reference to the accompanying figures. The foregoing may, however, be embodied in many different forms and should not be construed as limited to the illustrated embodiments set forth herein.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and, similarly, the term "and" should generally be understood to mean "and/or.".

Recitation of ranges of values herein are not intended to be limiting, referring instead individually to any and all values falling within the range, unless otherwise indicated herein, and each separate value within such a range is incorporated into the specification as if it were individually recited herein. The words "about," "approximately," or the like, when accompanying a numerical value, are to be construed as indicating a deviation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

In the following description, it is understood that terms such as "first," "second," and the like, are words of convenience and are not to be construed as limiting terms.

As used herein, unless otherwise indicated or made clear from the context, the term "physician" should be understood to include a surgeon preparing for and/or performing any one or more of the medical procedures described herein and, more broadly, should be understood to include any medical personnel, such as nurses, assisting a surgeon in preparing for or performing any one or more of the medical procedures described herein. Further, as used herein, the term "patient" shall be understood to include any type of mammal, including a human, on which a medical procedure such as, but not limited to a mastectomy and/or tissue harvesting, can be performed.

Further, as used herein, unless otherwise indicated or made clear from the context, the term "skin envelope" should be understood to refer to a three-dimensional volume defined by skin of the patient remaining following removal of tissue such as breast tissue. As an example, the three-dimensional volume defined by the skin envelope may receive an implant as part of certain types of reconstruction following a procedure such as a mastectomy. While the three-dimensional volume defined by the skin envelope may be usefully described in terms of the ability to receive an implant, it should be appreciated that, post-mastectomy, reconstruction using an implant is optional. That is, even in instances in which an implant is not used to reconstruct the breast following a mastectomy, a skin envelope is nevertheless formed by the removal of breast tissue.

Referring now to FIGS. 1-6, a system 100 for removal of tissue from a patient can include a cup 102, a cutting head 104, a controller 106, and a user interface 107. The cutting head 104 can be secured (e.g., releasably secured) to the cup 102 via a coupling 108 and can include, for example, an actuator 109 and a cutting tip 110. The controller 106 can be in one or more of electrical and mechanical communication with one or more of the cup 102, the cutting head 104, and the user interface 107 to control the actuator 109 and the cutting tip 110 to remove tissue along a three-dimensional contour 111 defined relative to the cup 102. In general, the system 100 can account for variations in breast size and shape during formation of a skin envelope as part of a mastectomy. More specifically, by accounting for three-dimensional complexity of the breast, the system 100 can advantageously reduce the time and likelihood of dimensional inaccuracy of skin envelope formation (e.g., thickness that is too thin or too thick in certain areas), as compared to skin envelopes formed using manual techniques. For the sake of clarity of explanation, the system 100 is generally described herein with respect to the removal of breast tissue as part of a mastectomy. Unless otherwise specified, or made clear from the context, it should be more generally understood that the system 100 can address challenges typically associated with manual techniques for excision of tissue in any one or more of various different procedures that are inherently three-dimensional in nature and of which a mastectomy is just one example. For example, the system 100 can address challenges associated with removing a substantially round cross-section (along or one or more planes) of tissue sufficiently pliable to be suctioned or otherwise conformed into a predetermined shape useful for precise excision of the tissue, as described in greater detail below. Further, or instead, unless otherwise specified or made clear from the context, it should be appreciated that any one or more of the devices, systems, and methods described herein can be used to facilitate allographic harvesting of skin from a cadaver, with such harvested skin being useful in certain types of reconstructive procedures, including certain types of breast reconstruction.

In use, as described in greater detail below, the cup 102 can be placed over a breast of a patient as part of a mastectomy, and the breast of the patient can be drawn toward the cup 102 through suction applied by a suction source 115 in fluid communication with the cup 102 such that skin along the breast conforms substantially to the cup 102. As also described in greater detail below, with skin along the breast substantially conforming to the cup 102, the controller 106 can control the actuator 109 to move the cutting tip 110 along the three-dimensional contour 111 at one or more predetermined distances from the cup 102. The cutting tip 110 can remove tissue along the three-dimensional contour 111 to form a skin envelope. That is, through conformation of the skin to the cup 102, the cup 102 can define a three-dimensional coordinate system that accounts for variations in breast size and shape and is, thus, useful for accurately positioning the cutting tip 110 to remove breast tissue along the three-dimensional contour 111.

The cup 102 can have at least one surface 112 defining a volume 114, a first opening 116, and a second opening 118. As used herein, the volume 114 of the cup 102 shall be understood to include a three-dimensional spatial region within which the breast tissue is to be separated from skin by the cutting tip 110 moving along the three-dimensional contour and, as a specific example, the volume 114 can extend from the first opening 116 to the second opening 118. In general, the volume 114 can be positionable about a breast of a patient with the at least one surface 112 of the cup 102 facing a skin surface of the breast, and the first opening 116 circumscribing the breast of the patient. The cutting head 104 can extend into the volume 114 through the second opening 118. With the volume 114 positioned about the breast of the patient and the first opening 116 circumscribing the breast of the patient, at least the cutting tip 110 can extend into the volume 114, and the actuator 109 can control movement of the cutting tip 110 within the volume 114.

The first opening 116 and the second opening 118 can be sized and oriented relative to one another in any of various different orientations suitable for, among other things, facilitating assembly of the system 100, for robust positioning of the cutting head 104 relative to the breast, and/or for suitably accommodating the size and shape of the breast of the patient. For example, the first opening 116 can have a first area and the second opening 118 can have a second area, with the first area generally being sized for circumscribing the breast and the second area generally being sized for facile manipulation by a physician to secure the cutting head 104 to the cup 102. Additionally, or alternatively, the first opening 116 and the second opening 118 can be substantially parallel to facilitate accurately positioning the cutting head 104 relative to the chest wall of the patient.

The at least one surface 112 of the cup 102 can provide one or more spatial boundaries within the volume 114 and, more specifically, can at least partially define a three-dimensional contour within the volume 114. In general, the actuator 109 can control movement of the cutting tip 110 along the three-dimensional contour 111 within the volume 114 to remove tissue within the volume 114. As used herein, the three-dimensional contour 111 within the volume 114 can include a set of three-dimensional spatial coordinates or other spatial references that, collectively, define an outline of a closed, three-dimensional shape within the volume 114. For example, the closed, three-dimensional shape can be derived from interpolation of a set of three-dimensional spatial coordinates.

The three-dimensional contour 111 can include a closed shape substantially similar to the shape of the volume 114, but spaced apart from the at least one surface 112 at one or more predetermined distances. Because the skin along the breast of the patient conforms to the at least one surface 112 of the cup 102 (e.g., through the application of a vacuum, as described in greater detail below) as the cutting tip 110 moves within the breast to remove tissue along the three-dimensional contour, it should be appreciated that the spacing between the at least one surface 112 of the cup 102 and the three-dimensional contour within the volume 114 generally corresponds to thickness of the skin envelope being formed during the mastectomy. Thus, to form a skin envelope of a desired thickness, the spacing between the at least one surface 112 of the cup 102 and the three-dimensional contour 111 within the volume 114 can be defined by one or more predetermined distances from the at least one surface 112 of the cup 102.

In certain implementations, the one or more predetermined distances can be fixed such that the resulting thickness of the skin envelope is also fixed (e.g., to facilitate compliance with a standard). In other instances, however, the one or more predetermined distances can be varied to account for differences in skin thickness between patients and/or to account for variations in skin thickness along the breast of a given patient. For example, the one or more predetermined distances between the three-dimensional contour 111 and the at least one surface 112 of the cup 102 can be input by a physician (e.g., through interaction with the user interface 107) as part of preparation for a mastectomy. It should be appreciated that the one or more predetermined distances input by the physician can be based on measurement and/or observation and, more generally, can facilitate formation of a skin envelope according to any one or more of a variety of clinical considerations associated with a reduced likelihood of complications.

The volume 114, the first opening 116, or both, can at least partially conform to a shape of the breast of the patient prior to the mastectomy. In general, it should be appreciated that an increased degree of conformity can facilitate controlling position of skin of the breast along the at least one surface 112 during a mastectomy. Thus, in certain instances, the cup 102 can be selected from one of a plurality of different predetermined sizes, with the selected size providing the highest degree of conformity between the at least one surface 112 of the cup 102 and skin of the breast of the patient. Continuing with this example, the plurality of different predetermined sizes can span variations in one or more dimensions to accommodate variations in breast size among the patient population. In some implementations, the cup 102 can be formed (e.g., molded) to conform to the specific size and shape of the breast of the patient.

In general, one or more of the volume 114 and the first opening 116 can have any one or more shapes having at least some degree of conformity with the breast of the patient. For example, one or more of the volume 114 and the first opening 116 can have certain symmetric features about one or more planes to approximate complementary symmetry of the breast. Such symmetric features can facilitate placement of the volume 114 relative to the breast and/or to facilitate positioning the cutting tip 110 within the volume 114. Additionally, or alternatively, such symmetric features can facilitate controlling dimensional tolerances of the volume 114 and, thus, dimensional tolerances of the skin envelope formed based on the volume 114. For example, one or more of the volume 114 and the first opening 116 can be symmetric about at least one plane 120 intersecting (e.g., perpendicular to) one or more of the first opening 116 and the second opening 118. Still further or instead, a cross-section of the volume 114 in at least one plane 122 parallel to the first opening 116 can be curvilinear, which can be useful for approximating contours of the breast. For example, the cross-section of the volume 114 in the at least one plane 122 parallel to the first opening 116 can be substantially elliptical (e.g., substantially circular).

In specific implementations, at least a portion of the volume 114 can be concave to at least partially envelop the breast. For example, a concave portion of the volume 114 can have a two-dimensional curvilinear profile (e.g., an arc) in the at least one plane 120 perpendicular to the first opening 116 to approximate a similar, complementary profile of the breast. As an additional or alternative example, the volume 114 can be shaped as a spherical dome having the first opening 116 as a base. A spherical dome can be useful, for example, for facilitating mapping the volume 114 to a spherical coordinate system. In certain instances, a spherical dome can provide a physician with a readily appreciable spatial framework for identifying the one or more predetermined distances defining the three-dimensional contour 111 along which the cutting tip 110 is moved.

Additionally, or alternatively, the at least one surface 112 of the cup 102 can be substantially rigid. More specifically, the at least one surface 112 can retain a predetermined shape upon exposure to vacuum pressure (e.g., a partial vacuum). As used herein, exposure to vacuum pressure should be understood to refer to a pressure below standard atmospheric pressure of 101.325 kPa. Thus, in use, the at least one surface 112 can retain a predetermined shape as vacuum pressure is applied between the at least one surface 112 and skin of the breast of the patient while an outer surface of the cup 102 is under atmospheric pressure. Continuing with this example, with the at least one surface 112 retaining the predetermined shape as the vacuum pressure is applied, the skin of the breast of the patient can be drawn toward the at least one surface 112. Because the at least one surface 112 remains in a fixed position, the skin of the breast of the patient can be reliably positioned along the at least one surface 112, thus facilitating removing breast tissue based on a three-dimensional coordinate system defined by the predetermined shape of the at least one surface 112.

In some implementations, the at least one surface 112 of the cup 102 can include a textured pattern. In general, the textured pattern can resist relative movement between the at least one surface 112 and skin in contact with the at least one surface 112. The textured pattern can include, for example, a plurality of bumps, undulations, or other structural features extending in a direction toward the volume 114.

Additionally, or alternatively, an adhesive can be disposed along the at least one surface 112 of the cup 102 to facilitate retaining skin of the breast of the patient in a fixed position in contact with the at least one surface 112 of the cup 102 throughout a mastectomy. For example, the adhesive can be disposed along only a portion of the at least one surface 112 of the cup 102. As compared to using the adhesive along the entirety of the at least one surface 112 of the cup 102, using the adhesive along only a portion of the at least one surface 112 can facilitate separating the at least one surface 112 of the cup 102 from skin of the breast of the patient following the mastectomy. Further, or instead, the adhesive can include a cooling gel and, more generally, can carry heat away from the surface of the skin to mitigate the impact of heat that may be generated by operation of the cutting tip 110 in certain implementations.

The coupling 108 can be disposed on the cup 102 and, in general, can be releasably securable to the cutting head 104 to establish sealed fluid engagement between the cup 102 and the cutting head 104. The coupling 108 can be adjacent to the second opening 118 of the cup 102 to facilitate securing the coupling 108 to the cutting head 104 with the cutting head 104 positioned through the second opening 118 of the cup 102. For example, the coupling 108 can include one or more features to facilitate moving the cutting head 104 through the second opening 118 as the system 100 is prepared for a mastectomy.

The releasable engagement between the coupling 108 and the cutting head 104 can be useful, for example, for separating the cup 102 from the cutting head 104, as can be advantageous for replacing the cup 102 between procedures. Additionally, or alternatively, separating the cup 102 from the cutting head 104 can be useful for selecting a size of the cup 102 appropriate for the patient (e.g., selecting the size of the cup 102 from a plurality of predetermined sizes of the cup and/or selecting a cup 102 customized to match the size and shape of the breast of the patient). As used herein, the sealed engagement between the coupling 108 and the cutting head 104 can include substantially sealed fluid communication such that biological material does not pass through the second opening 118 as the cutting tip is used to separate tissue from skin during a procedure.

The sealed engagement between the at least one portion of the coupling 108 and the cutting head 104 should be understood to facilitate the establishment of at least a partial vacuum between the cup 102 and skin along the breast of the patient during the mastectomy. That is, with the coupling 108 and the cutting head 104 in sealed engagement and with the first opening 116 circumscribing the breast of the patient and the cup 102 positioned along the chest wall of the patient, suction can be applied through a suction lumen 119 defined by the cutting head 104 and in fluid communication with the suction source 115. Suction applied in this way can form at least a partial vacuum in the volume 114 between skin of the breast of the patient and the at least one surface 112 of the cup 102. With the cup 102 formed of a sufficiently rigid material, the at least one surface 112 of the cup 102 can remain substantially nondeformed in the presence of the suction and skin of the breast of the patient can be drawn toward the at least one surface 112 of the cup 102. The result, therefore, of application of suction by the suction source 115 is that skin of the breast of the patient is drawn toward the at least one surface 112 of the cup 102 in a predictable and repeatable manner. Thus, as described in greater detail below, suction applied by the suction source 115 can be useful for addressing the three-dimensional challenges associated with accurately forming a skin envelope as part of a mastectomy.

In general, the coupling 108 can include one or more mechanical features engageable with one or more complementary features of the cutting head 104. More generally, the coupling 108 can be releasably securable to the cutting head 104 through any of various different known mechanical connections. For example, the coupling 108 and the cutting head 104 can include complementary threaded features such that the cup 102 can be connected to the cutting head 104 by screwing the coupling 108 to complementary grooves defined by the cutting head 104. Additionally, or alternatively, the coupling 108 and the cutting head 104 can be securable to one another via any one or more of an interference fit, complementary magnetic materials, a clip, etc.

The cup 102 can, further or instead, include a transmitter 124 disposed along the cup 102. The transmitter 124 can include information related to the cup 102, such as information useful for preparing the system 100 for use in performing a mastectomy. The information associated with the transmitter 124 can include, for example, information related to safety. In use, the information related to the cup 102 can be transmitted from the transmitter 124 to the controller 106, where the information can be used as part of setting up the system 100.

In certain implementations, the transmitter 124 can include information related to verification of a source of the cup 102. Such information related to the source of the cup 102 can include, for example, a proprietary code useful for verifying that the cup 102 is a genuine part intended for use with the system 100. Further, or instead, the transmitter 124 can include information related to previous use of the cup 102. For example, the transmitter 124 can include a counter incrementable upon each connection of the cup 102 to the cutting head 104. Such information regarding previous use of the cup 102 can increase the likelihood of compliance with regulations and/or guidelines associated with reuse of the cup 102. As an example, upon connecting the cup 102 to the cutting head 104, the information related to the number of uses of the cup 102 can be transmitted to the controller 106 for verification (e.g., on a central database in communication with the controller 106) that the cup 102 is in compliance with regulations regarding previous use (e.g., that the cup 102 has not been previously used).

In some implementations, the transmitter 124 can include size information related to the cup 102. The size information can correspond to the size and shape of the volume 114 of the cup 102. More specifically, the size information can include three-dimensional coordinates and/or dimensions of the at least one surface 112 of the cup 102. The size information can be transmitted to the controller 106 and, as described in greater detail below, the controller 106 can limit movement of the cutting tip 110 within the volume 114 of the cup 102 based on the size information received from the transmitter 124.

The transmitter 124 can be activatable to transmit the information related to the cup to a remote receiver, such as the controller 106. For example, the transmitter 124 can include a passive RFID tag and, in use, electromagnetic energy directed to the passive RFID tag can activate the passive RFID tag to transmit the information from the transmitter 124 to the controller 106. As a specific example, the electromagnetic energy can be transmitted to the passive RFID tag from the cutting head 104 coupled to the cup 102. In general, the passive RFID tag, or other similar passive techniques for storing and transmitting information from the cup 102 to the controller 106, can facilitate forming the cup 102 as a limited-use component (e.g., a single-use component or some other predetermined number of uses). A limited-use component can reduce the likelihood of complications associated with unintended deformation or damage of the cup 102 through repeated uses, such as may occur over the course of a large number of uses.

The system 100 can, in some instances, include a gasket 126 disposed along the first opening 116 of the cup 102 and, in use, the gasket 126 can be in contact with skin of the patient along the chest wall. The gasket 126 can be formed of a material differing from the material forming one or more portions of the cup 102 to provide certain mechanical advantages. For example, the gasket 126 can be formed of a pliable material (e.g., silicone, rubber, or a combination thereof), such as a material that is more pliable than the material along the at least one surface 112 of the cup. The pliability of the gasket 126 can, in some instances, provide mechanical resistance to inadvertent movement of the cup 102 along skin of the patient during a procedure. Additionally, or alternatively, the gasket 126 can be pliable to at least partially conform to the chest wall of the patient to provide at least a partial fluid seal between the cup 102 and the chest wall. Continuing with this example, the seal provided by the gasket 126 can facilitate the formation of at least a partial vacuum useful for drawing skin along the breast of the patient toward the at least one surface 112 of the cup 102.

In certain implementations, the gasket 126 can be releasably positionable along the first opening 116. That is, the gasket 126 can be positioned along the first opening 116 of the cup 102 prior to a procedure. Such releasable positioning of the gasket 126 can facilitate separate sterilization of the gasket 126 and the cup 102, which can be useful, for example, in instances in which the gasket 126 is formed of a material sterilizable according to a technique that is incompatible with sterilization of material forming the cup 102. Additionally, or alternatively, the releasable positioning of the gasket 126 on the cup 102 can be useful for selecting a material that is less likely to irritate skin of a given patent (e.g., in instances in which the patient may have a sensitivity, such as an allergy, to a given type of material).

In general, the cutting tip 110 can be positionable along the breast of the patient to separate tissue. More specifically, the cutting tip 110 can be positionable along the three-dimensional contour 111 to separate the tissue to be removed from the that tissue that will remain to form the skin envelope. The separation of the tissue in this manner can be achieved, for example, through the application of any one or more forms of energy that can be locally controlled along the three-dimensional contour 111. Thus, for example, the cutting tip 110 can be actuatable to apply any manner and form of mechanical energy, thermal energy, electrical energy, chemical energy, and combinations thereof to separate the tissue. For the sake of clarity of explanation, however, the cutting tip 110 is described below in the context of electrosurgery, which can offer any of various different advantages in the formation of a breast envelope. Examples of advantages of electrosurgery using the cutting tip 110 include, but are not limited to, separation of tissue while controlling bleeding, formation of the cutting tip 110 with a form factor suitable for movement within the volume 114 defined by the at least one surface 112 of the cup 102, and local control of energy with a low likelihood of collateral tissue damage.

The cutting tip 110 can include a resistance element 128, which can be any of various different shapes suitable for maneuverability along the three-dimensional contour 111 over the course of a mastectomy. For example, the resistance element 128 can be substantially needle-like. Further, or instead, the resistance element 128 can be formed of any one or more of various different sterilizable, biocompatible, and highly conductive materials, of which stainless steel is one example. The resistance element 128 may, additionally or alternatively, include a coating, such as may be useful for reducing the likelihood of adhesion of tissue to the resistance element 128. Thus, for example, the resistance element 128 can include a polytetrafluoroethylene coating (e.g., Teflon™, available from The Chemours Company of Wilmington, Del.).

In certain implementations, the resistance element 128 can be an electrode (e.g., monopolar or bipolar) positionable into electrical contact with tissue along the three-dimensional contour 111. The resistance element 128 can be in electrical communication with the controller 106 and, in use, the controller 106 can generate and control electrical energy (e.g., in the form of high frequency alternating current, such as RF electrical energy) to be passed into the tissue via contact between the tissue and the resistance element 128. The energy delivered into the tissue through the resistance element 128 can vaporize or otherwise destroy the tissue locally to form an incision. Additionally, or alternatively, the energy delivered to the tissue through the resistance element 128 can coagulate the tissue, which can be useful for reducing blood loss from the patient.

The cutting tip 110 can define a track 130, and the resistance element 128 can be movable back and forth along the track 130. For example, electrical energy can be delivered to the tissue via the resistance element 128 as the resistance element 128 moves back and forth along the track 130. Moving the resistance element 128 along the track 130 as electrical energy is delivered to the tissue can be useful for removing tissue through application of a plurality of slices along the three-dimensional contour 111. Slicing in this way can advantageously facilitate following the three-dimensional contour 111, as the angle of orientation of each slice can be varied as necessary to conform to the three-dimensional contour 111.

In some implementations, the cutting tip 110 can include one or more sensors 132 in electrical communication with the controller 106. The one or more sensors 132 can be, for example, adjacent to the resistance element 128 to an extent sufficient to measure one or more physical parameters in the vicinity of the resistance element 128. As described in examples below, the one or more physical parameters measured by the one or more sensors 132 can be useful for positioning the cutting tip 110 and/or for controlling energy delivery to the resistance element 128.

The one or more sensors 132 can advantageously include one or more position sensors to sense a distance from the cutting tip 110 to the at least one surface 112 of the cup 102 defining the volume 114 and the first opening 116. As should be readily understood, because the cup 102 remains stationary with respect to the breast (e.g., through suction or other forces holding the cup 102 in contact with skin of the breast) and the three-dimensional contour 111 is defined by one or more predetermined distances from the at least one surface 112 of the cup 102, the sensed distance from the cutting tip 110 to the at least one surface 112 of the cup 102 can be advantageously used as feedback for positioning the cutting tip 110 to form a skin envelope along the three-dimensional contour 111. In certain implementations one or more position sensors can be useful for repositioning the cutting tip 110 to specific coordinates along the three-dimensional contour 111, such as in the event of an interruption in the mastectomy. Thus, more generally, the cup 102 can define a local coordinate system, and the one or more sensors 132 can provide feedback useful for positioning the cutting tip 110 along such a coordinate system.

The one or more sensors 132 can include any of various different sensors suitable for sensing the position of the cutting tip 110 relative to the at least one surface 112 of the cup 102. As an example, the one or more sensors 132 can include a magnetic position sensor responsive to a magnetic field generated by one or more magnetic elements carried in or on the cup 102 to determine a position of the one or more sensors 132. Further or instead, the one or more sensors 132 can include an optical sensor, an acoustic sensor, or a combination thereof. In certain implementations, the cup 102 can carry one or more elements useful as a landmark detectable by the one or more sensors 132. For example, in implementations in which the one or more sensors 132 include an optical sensor, the cup 102 can include a band of optically opaque material demarcating a boundary relative to the chest wall to reduce the likelihood of inadvertently moving the cutting tip 110 into contact with the chest wall, where manual dissection of tissue may be desirable.

In some instances, the one or more sensors 132 can include one or more tissue sensors useful for detecting whether the cutting tip 110 is in contact with tissue. An example of a tissue sensor is a pressure sensor positionable to detect contact pressure (e.g., through use of a strain gauge or other similar method) between the cutting tip 110 and tissue. An additional or alternative example of a tissue sensor is a capacitance sensor, with a change in capacitance being indicative of contact between the cutting tip and tissue.

Detecting contact between the cutting tip 110 and the tissue at the treatment site can be useful, for example, for tracking progress of the formation of the skin envelope along the three-dimensional contour 111. Further, or instead, detecting contact between the cutting tip 110 and tissue along the three-dimensional contour 111 can be useful for efficiently achieving proper orientation of the cutting tip 110 along the three-dimensional contour 111. As an example, the actuator 109 can move the cutting tip 110 according to one or more predetermined progressions of movement until the one or more sensors 132 detect contact with tissue, thus indicating that the cutting tip 110 is in a suitable position for cutting tissue along the three-dimensional contour 111. Still further or instead, detecting contact between the one or more sensors 132 and tissue can serve as a basis for enabling or disabling delivery of electrical energy to the resistance element 128, which can reduce the likelihood of unintended tissue damage.

In some implementations, the one or more sensors 132 can include a blood sensor, examples of which include any of various different sensors known in the art for detecting the presence of blood in a surgical setting and, thus, include an optical sensor, an acoustic sensor, an impedance sensor, or combinations thereof. A blood sensor carried on the cutting tip 110 can be useful, for example, for detecting proper placement of the cutting tip 110 along the skin envelope being formed along the three-dimensional contour 111. Additionally, or alternatively, the blood sensor can be useful as a feedback parameter for controlling coagulation along the skin envelope.

In certain implementations, the one or more sensors 132 can include a temperature sensor, such as a thermocouple. The temperature sensor can be useful for detecting contact between the cutting tip 110 and tissue, with a change in temperature being indicative of contact. Further, or instead, the temperature sensor can be useful for providing feedback regarding the progress of the incision and/or coagulation along the skin envelope being formed along the three-dimensional contour 111.

Additionally, or alternatively, the one or more sensors 132 can include a moisture sensor. The moisture sensor can be useful for detecting whether the cutting tip 110 is in a fluid, such as blood or saline. In some instances, the presence of moisture can be a useful indicator that the cutting tip 110 is positioned in an environment in which energy can be safely delivered to the cutting tip 110. For example, the detected moisture can act as a medium for dissipating energy delivered to the cutting tip 110, with such energy dissipation being generally useful for protecting tissue that is beyond an area targeted by the cutting tip 110.

In some implementations, the one or more sensors 132 can include a combination of sensors such that the cutting tip 110 is a blood-seeking tip. As an example, in instances in which the one or more sensors 132 include a blood sensor, a temperature sensor, and a moisture sensor, the signals received from these one or more sensors 132 can be combined to provide an indication of a direction in which the cutting tip 110 is more likely to encounter blood. In the context of formation of a skin envelope along the three-dimensional contour 111, the tissue to be targeted along the three-dimensional contour 111 at a given time-step is generally characterized by blood as the tissue is separated from skin forming the skin envelope. That is, the skin envelope is formed through a progression of cuts, with the position of the next cut in the progression being characterized by the presence of blood. Thus, instances in which the cutting tip 110 is a blood-seeking tip, feedback from the one or more sensors 132 can provide a basis for actuating one or both of the pivot arm 136 and the extension arm 138 to position the cutting tip 110 in the vicinity of blood. Automated or semi-automated movement of the cutting tip 110 in a blood-seeking manner can be useful, for example, for achieving efficient movement of the cutting tip 110 relative to the three-dimensional contour 111 as the skin envelope is formed.

The cutting tip 110 can, in certain instances, define one or more suction channels 134 adjacent to the resistance element 128. The one or more suction channels 134 can be useful, for example, for removing vapor, coagulated matter, or other material formed or otherwise present as electrical energy is directed from the resistance element 128 to tissue. Such suction can be useful, for example, for reducing the likelihood that extraneous material will interfere with forming an incision through contact between the resistance element 128 and tissue. In use, the one or more suction channels 134 can be in fluid communication with a suction source, such as wall suction typically available in an operating room. Further or instead, the one or more suction channels 134 can be coupled to a suction source that is regulated to provide a controlled amount of suction, such as to provide suction based on whether electrical energy is being delivered to the resistance element 128.

In general, the actuator 109 can be in electrical communication with the controller 106 and controllable to move the cutting tip 110 along the three-dimensional contour 111. For example, the actuator 109 can move the cutting tip 110 parallel to the at least one surface 112 of the cup 102. Further or instead, the actuator 109 can move the cutting tip 110 to orient the resistance element 128 in a particular manner (e.g., tangential) relative to the three-dimensional contour 111 along which the skin envelope is to be formed. Unless otherwise specified or made clear from the context, it should be appreciated that the actuator 109 can be controlled to move the cutting tip 110 based at least in part on feedback from the one or more sensors 132.

In certain implementations, the actuator 109 can be actuatable to move the cutting tip 110 through at least three degrees of freedom within the volume 114 defined by the at least one surface 112 of the cup 102. For example, the actuator 109 can include a pivot arm 136 and, additionally or alternatively, an extension arm 138 moveable in coordination with one another to move the cutting tip 110 along the three-dimensional contour 111. While movement of the cutting tip 110 is described below with respect to actuation of the actuator 109 and actuation of the pivot arm 136, it should be appreciated that such description is for the sake of clarity of explanation and that the actuator 109 can include any manner and number of members actuatable to achieve any manner and form of movement of the cutting tip 110 within the volume 114. Thus, in certain instances, the actuator 109 can include additional or alternative members suitable for moving the cutting tip 110 along a plurality of degrees of freedom (e.g., six degrees of freedom) within the volume 114.

The pivot arm 136 can be rotatable about a first axis 140 defined by the pivot arm 136 to control a position of the cutting tip 110 in the at least one plane 122 parallel to the first opening 116. For example, the pivot arm 136 can include an electric rotary actuator or other similar actuator for converting electrical energy to mechanical energy for rotating the pivot arm 136. In general, the pivot arm 136 can be coupled to the extension arm 138 such that rotation of the pivot arm 136 results in rotation of the extension arm 138.

The extension arm 138 can be axially moveable along a second axis 142 defined by the extension arm 138. For example, the extension arm 138 can include telescoping portions moveable relative to one another along the second axis 142 to change a length of the extension arm 138 along the second axis 142. The extension arm 138 can include a linear actuator or other similar actuator) for converting electrical energy to mechanical energy to change the length of the extension arm 138 along the second axis 142.

In certain implementations, the pivot arm 136 and the extension arm 138 can be moveable relative to one another to change an included angle θ between the first axis 140 and the second axis 142. For example, the extension arm 138 can be rotatable in at least one direction about a pivot joint 144 between the pivot arm 136 and the extension arm 138. The pivot joint 144 can include an electric rotary actuator or other similar actuator for converting electrical energy to mechanical energy for changing the included angle θ between the first axis 140 and the second axis 142.

While movement of the extension arm 138 in the volume 114 can be achieved through a combination of actuators disposed along the extension arm 138 to apply force directly to the extension arm 138, it should be appreciated that other types of actuation of the extension arm 138 are additionally or alternatively possible. For example, given size constraints associated with the volume 114, actuation components may be advantageously positioned outside of the volume 114. As described in greater detail below, a combination of springs, cables, or other similar mechanical components can be used along with or instead of the actuation components to position the extension arm 138.

The extension arm 138 can be substantially rigid to resist deformation under typical forces experienced by the extension arm 138 as the cutting tip 110 is moved along and positioned relative to the three-dimensional contour 111 to remove tissue. That is, the extension arm 138 can be substantially rigid under a variety of states of telescoping extension required to position the cutting tip 110 relative to the three-dimensional contour 111. Thus, for example, the extension arm 138 can be substantially rigid such that, under forces exerted on the extension arm 138 by any of various different actuators and/or tissue during a procedure, the position of the extension arm 138 (and, thus, the position of the cutting tip 110) remains within an error tolerance acceptable for a given procedure, which can be less than about ±0.5 mm for certain procedures and, more specifically, can be completely rigid for certain procedures. Accordingly, with little or no movement of the extension arm 138 in response to forces exerted on the extension arm 138, it should be appreciated the substantial rigidity of the extension arm 138 can be useful for facilitating accurate determination of a position of the cutting tip 110.

In general, the controller 106 can include one or more processors 148 and a non-transitory, computer readable storage medium 150. The controller 106 can be in electrical communication at least with the actuator 109 and the cutting tip 110. The computer readable storage medium 150 can have stored thereon computer executable instructions for causing the one or more processors to carry out any one or more of the methods described herein for dissecting tissue along the three-dimensional contour 111 to form a skin envelope. Further, or instead, the computer readable storage medium 150 can have stored thereon computer executable instructions for causing the one or more processors to carry out any one or more of the methods described herein for identifying one or more features of the cup 102 coupled to the cutting head 104. Still further or instead, the computer readable storage medium 150 can have stored thereon computer executable instructions for causing the one or more processors to receive at least one user input (e.g., through the user interface 107), with the user input corresponding to any of various different parameters useful for accurate formation of a skin envelope. Examples of such parameters can include, without limitation, information regarding the size and/or shape of the cup 102 and, further or instead, can include one or more predetermined distances from the at least one surface 112 of the cup 102 defining the volume 114 and the first opening 116.

Figure 7:
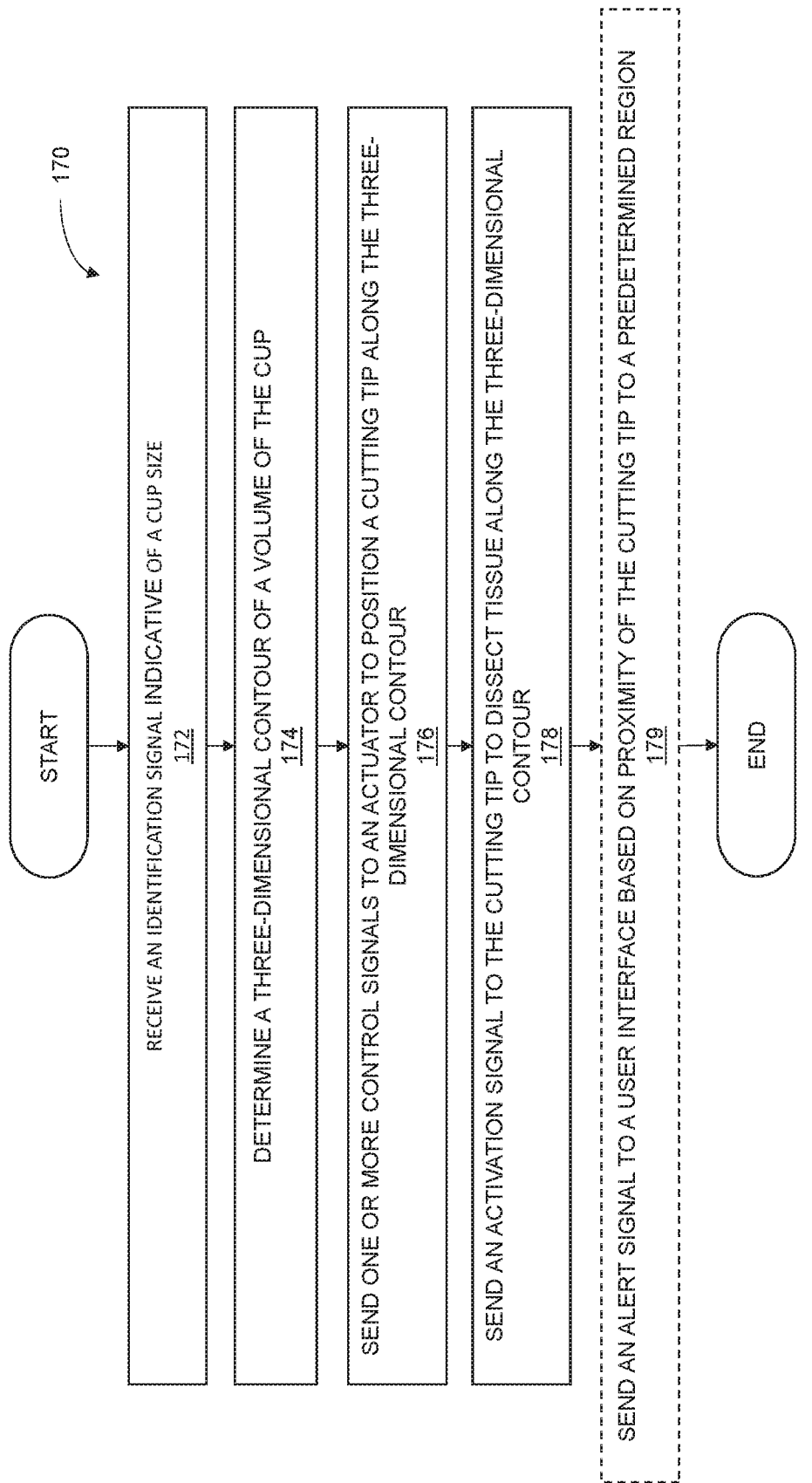
FIG. 7 is a flowchart of an exemplary method of controlling three-dimensional dissection of tissue.

FIG. 7 is a flowchart of an exemplary method 170 of removing tissue from a patient. Unless otherwise specified or made clear from the context, it should be appreciated that the exemplary method 170 can be carried out using any one or more of the devices, systems, and methods described herein. Thus, for example, the exemplary method 170 can be carried out by the controller 106 (FIG. 1) and, more specifically, can be implemented as instructions stored on the computer readable storage medium 150 (FIG. 1) and carried out by the one or more processors 148 (FIG. 1).

The exemplary method 170 can include receiving 172 an identification signal indicative of a size of a cup defining a volume, determining 174 a three-dimensional contour within the volume of the cup, sending 176 one or more control signals to an actuator to position a cutting tip along the three-dimensional contour, and sending 178 an activation signal to the cutting tip to dissect tissue along the three-dimensional contour to form at least a portion of a skin envelope. As described in greater detail below, determining 174 the three-dimensional contour can be based on the received 172 identification signal indicative of the size of the cup. Accordingly, among other advantages, the exemplary method 170 can be useful for reliably accommodating three-dimensional variations that exist among breasts in a patient population, thus facilitating improved accuracy of skin envelopes formed during mastectomies.

In general, receiving 172 the identification signal indicative of the size of the cup can include receiving any manner and form of signal associated with the cup. Thus, as used herein, the identification signal can include any manner and form of electrical signal, optical signal, mechanical signal, or combination thereof, derived from information or features associated with (e.g., carried on) the cup. The identification signal indicative of the size of the cup can be useful, for example, for setting one or more boundary conditions for movement of the cutting tip during a mastectomy. That is, the cup can be selected from among a plurality of sizes such that the volume defined by the cup can substantially match the size of the breast of the patient, and the identification signal can provide a controller with relevant size information associated with the cup selected for a given procedure. Further, or instead, the identification signal indicative of the size of the cup can be useful in combination with one or more other signals (e.g., a manual input through a user interface) for the purpose of size verification or verification of other information such as authentication of the cup as a genuine part meeting, among other criteria, size tolerances, material properties, etc.

In certain implementations, receiving 172 the identification signal can include sending an interrogation signal to the cup. For example, the interrogation signal can be sent from the cutting head, or another reusable portion of the system, to the cup (e.g., upon establishing a mechanical connection between the cutting tip and the cup). The interrogation signal can include any one or more of an electrical signal, an optical signal, and a mechanical signal. Thus, for example, the interrogation signal can include an RF signal directed to a passive RFID tag carried on the cup according to any one or more of the various different methods described herein.

The identification signal can include, in some instances, information indicative of use history of the cup. For example, the use history of the cup can be stored on the cup itself. Additionally, or alternatively, the use history of the cup can be stored in a database on the controller, at a remote server, or a combination thereof. The identification signal can include a unique identifier of the cup (e.g., a serial number), and the use history of the cup can be updated upon receiving the identification signal (e.g., in response to an interrogation signal or otherwise detecting a connection between the cup and the cutting head). In certain applications, it can be desirable to limit the number of uses of the cup (e.g., to reduce the likelihood of unintended failure or deformation of the cup). Thus, in certain instances, sending 176 the one or more control signals to the actuator can be based on whether the use history of the cup is below a predetermined threshold. By way of example, in the case of single-use devices, it should be understood that the threshold is one such that, upon subsequent connection of the cup following a single use, sending 176 the one or more control signals can be blocked until the cup is replaced with a new cup.

In general, the three-dimensional contour can be determined 174 based on the received 172 identification signal indicative of the size of the cup. That is, the identification signal can provide location information regarding the at least one surface defining the volume of the cup, and the three-dimensional contour can be defined relative to the known position of the at least one surface. With skin of the breast held against the at least one surface defining the volume of the cup (e.g., through suction, an adhesive, or a combination thereof), spacing between the three-dimensional contour and the at least one surface defining the volume of the cup substantially defines the thickness of the skin envelope formed according to the exemplary method 170. Thus, it should be appreciated that determining 174 the three-dimensional contour based on the received 172 identification signal indicative of the size of the cup can be useful for efficiently and reliably accounting for variations in three-dimensional anatomical structures—with such variations being characteristic of breasts in the patient population.

The spacing between the three-dimensional contour and the at least one surface defining the volume of the cup can be implemented according to any one or more of the techniques described herein. Thus, for example, the three-dimensional contour can be parallel to and spaced apart from the at least one surface of the cup. Additionally, or alternatively, the three-dimensional contour can be spaced apart from the at least one surface of the cup at one or more predetermined distances. Further, or instead, determining 174 the three-dimensional contour within the volume can include receiving one or more predetermined distances from an input device operated by the physician.

In general, sending 176 the one or more control signals to the actuator coupled to the cutting tip can include any combination of control signals associated with positioning the cutting tip. As used herein, positioning the cutting tip should be understood to include locating the cutting tip along the three-dimensional contour, orienting the cutting tip relative to the three-dimensional contour, or a combination thereof. More specifically, given the three-dimensional nature of the skin envelope being formed, it is generally desirable to send one or more control signals to locate the cutting tip along three-dimensional contour in a specific orientation at the given location. That is, a combination of location and orientation of the cutting tip can be controlled to remove tissue along a complex geometry with little or no collateral damage to tissue forming the skin envelope.

In some applications, the cutting tip can be oriented to dissect tissue in a direction tangential to the three-dimensional contour at a given location. As used herein, tangential shall be understood to include geometrically tangential orientations as well as orientations deviating slightly from the geometric ideal but that would nevertheless be understood by a person of ordinary skill in the art to be tangential to the three-dimensional contour within the typical dimensional resolution of electromechanical control. Thus, for example, it should be understood that the cutting tip can define a tip axis (e.g., extending through a resistance element of the cutting tip), and the one or more control signals sent 175 to the actuator can position the tip axis tangent to the three-dimensional contour. Orienting the cutting tip in a direction tangential to the three-dimensional contour can be a particularly useful solution for controlled dissection of tissue along a three-dimensional contour, as a plurality of tangential dissections can be executed in sequence to approximate the three-dimensional contour along which the skin envelope is sought to be formed.

In certain implementations, the actuator can have at least three degrees of freedom, and sending 176 the one or more control signals to the actuator can include sending a respective control signal associated with each of the three degrees of freedom of the actuator for movement along each axis of a three-dimensional coordinate system. It should be readily understood that additional control signals can be associated with additional degrees of freedom. Thus, for example, additional degrees of freedom can be associated with rotation about each axis of a three-dimensional coordinate system (e.g., roll, pitch, and yaw).

Sending 178 the activation signal to the cutting tip to dissect tissue along the three-dimensional contour can include sending the signal according to any one or more of various different control criteria. In particular, because sending 178 the activation signal can be based on an automated or a semi-automated process, it should be understood that control criteria useful for reducing the likelihood of damage to collateral tissue or other complications can be particularly useful. For example, sending 178 the activation signal can include selectively sending the activation signal, such as upon determination that the cutting tip is appropriately positioned along the three-dimensional contour. Continuing with this example, the determination of whether the cutting tip is appropriately positioned along the three-dimensional contour can be based on feedback from any one or more of the different types of sensors described herein.

The exemplary method 170 can, in some cases, include sending 179 an alert signal to a user interface based on proximity of the cutting tip to a predetermined region of the volume. For example, in certain applications, aspects of controller-based dissection using the devices, systems, and methods described herein can be combined with those of conventional manual dissection as necessary or desirable. That is, while controller-based control of movement and selective activation of the cutting tip can be useful for precise removal of tissue along certain areas of the breast, conventional manual dissection may be preferable and/or more effective along other areas of the breast. Sending 179 the alert to the user interface, therefore, can be useful for alerting the physician that a controller-based portion of the mastectomy is complete or nearing completion, and that the remainder of the mastectomy can be carried out by the physician.

The chest wall presents a specific example of a region that may benefit from transitioning from controller-based dissection to manual dissection. Unlike the three-dimensional contour along the skin envelope, dissection along the chest wall is substantially two-dimensional. Such two-dimensional dissection present challenges with respect to, among other things, access by automated devices or systems. Further, two-dimensional dissection along the chest wall is particularly well-suited to manual dissection techniques carried out by a physician using conventional dissection tools, given the well-defined areolar plane that exists between the breast and the chest wall (pectoralis major muscle fascia). Accordingly, it may be desirable to transition from a controller-based dissection process to a manual dissection process at a predetermined distance from the chest wall. That is, continuing with this example, sending 179 the alert to the user interface can provide an indication to the physician that dissection is complete to within a predetermined distance from the chest wall. The physician can then complete the mastectomy using manual dissection techniques along a substantially two-dimensional profile.

Figure 8:
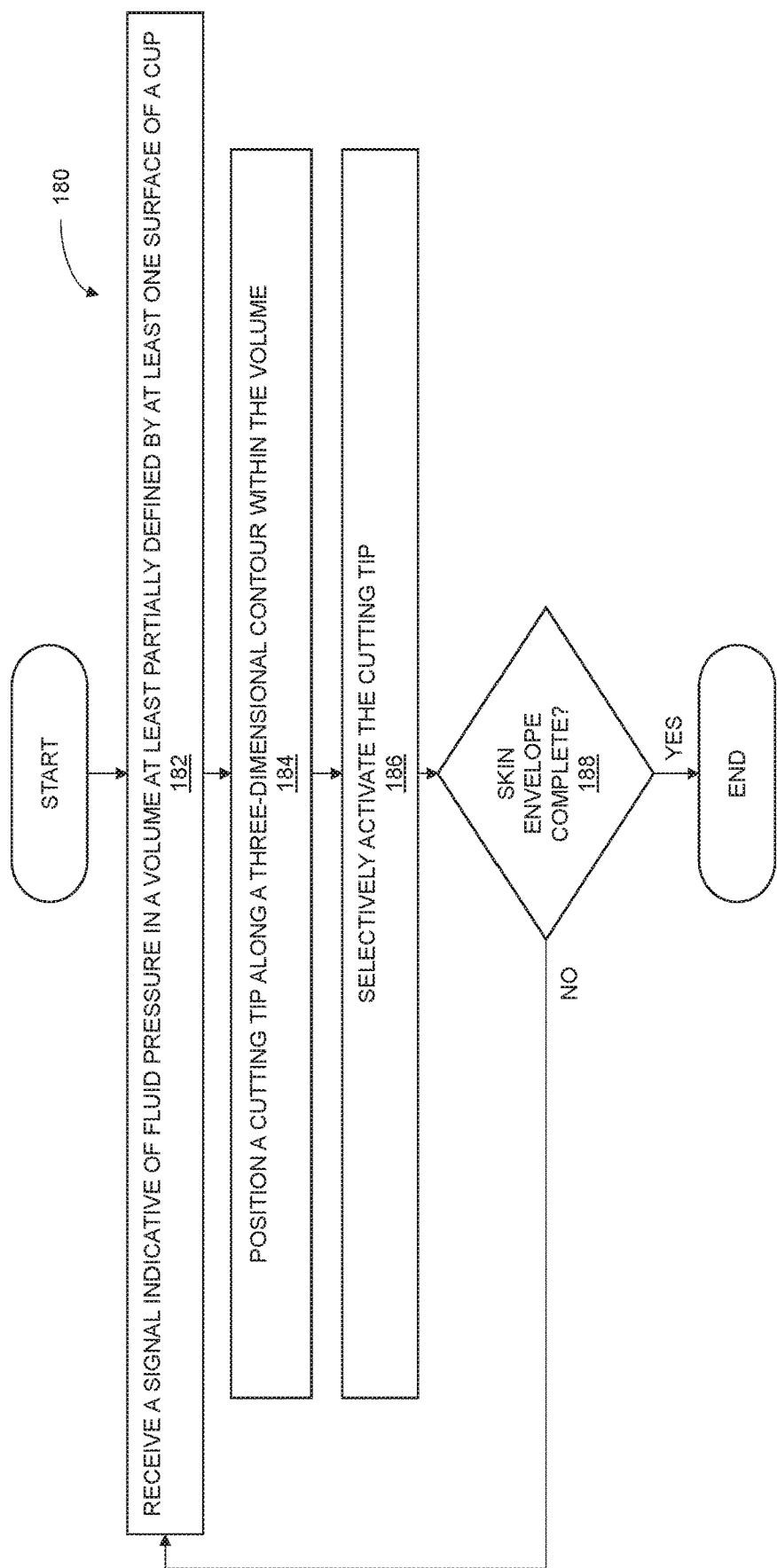
FIG. 8 is a flowchart an exemplary method of vacuum-based anchoring of three-dimensional dissection of tissue.

FIG. 8 is a flowchart an exemplary method 180 of vacuum-based anchoring for three-dimensional dissection of tissue. Unless otherwise specified or made clear from the context, it should be appreciated that the exemplary method 180 can be carried out using any one or more of the devices, systems, and methods described herein. Thus, for example, the exemplary method 180 can be carried by the controller 106 (FIG. 1) and, more specifically, can be implemented as instructions stored on the computer readable storage medium 150 (FIG. 1) and carried out by the one or more processors 148 (FIG. 1).

The exemplary method 180 can include receiving 182 a signal indicative of fluid pressure in a volume at least partially defined at least one surface of a cup, positioning 184 a cutting tip along a three-dimensional contour within the volume (e.g., the three dimensional contour can be spaced apart from the at least one surface of the cup at one or more predetermined distances), and selective activation 186 of the cutting tip to dissect tissue of a patient along the three-dimensional contour. As described in greater detail below, selective activation 186 of the cutting tip can be based on the received 182 signal indicative of fluid pressure in the volume. Accordingly, the exemplary method 180 can make beneficial use of pressure—more specifically, vacuum pressure—in the volume to draw skin of the breast into a known, three-dimensional profile at the surface of the cup and maintain the skin of the breast in this known, three-dimensional profile as the tissue is dissected to form a skin envelope. That is, the exemplary method 180 can make use of vacuum pressure to facilitate achieving robust and repeatable three-dimensional positioning of skin of the breast as a skin envelope is formed.

In general, receiving 182 the signal indicative of fluid pressure in the volume can include receiving any one or more of various different signals indicative of pressure in the volume with the cup disposed about a breast of the patient and breast of the patient extending into the volume. Thus, for example, the signal indicative of the fluid pressure in the volume can be a signal received from a pressure sensor in the volume. As an example, one or more sensors on the cutting tip (e.g., the one or more sensors 132 on the cutting tip 110 in FIG. 6) can include a pressure sensor, which may be useful for confirming that there is sufficient vacuum pressure locally within the volume and, more specifically, locally in the vicinity of where the next cut in a progression of cuts will take place. While overall pressure in the volume and a local pressure in a portion of the volume may typically be the same, conditions may arise during the formation of a skin envelope that can cause the local pressure to deviate from a global pressure. For example, one or more portions of the volume may become blocked from a vacuum source as the skin envelope is formed and, under such conditions, the pressure in the volume may vary. Accordingly, a local measurement of pressure in the vicinity of the cutting tip can be a useful safeguard against unintended variations in pressure. Additionally, or alternatively, receiving the signal indicative of fluid pressure in the volume can include receiving a signal from a pressure sensor outside of the volume in fluid communication and/or in mechanical communication with the volume to provide an indication of global pressure in the volume. In certain instances, receiving 182 the signal indicative of the pressure can include receiving a signal from one or more sensors.

In certain implementations, the signal indicative of the fluid pressure in the volume can be received 182 over a predetermined period of time (e.g., a moving temporal window). The predetermined period of time can be useful, for example, accounting for variations in pressure, such as variations in pressure that may occur in instances in which operating room suction is used as at least a portion of the suction applied to the volume defined by the at least one surface of the cup. In certain instances, selective activation 186 of the cutting tip may be based on a fluctuation of the received pressure signal over the predetermined period of time. Such a fluctuation may be indicative of, for example, an undesirable transient condition, which may result in movement of skin of the patient. Thus, continuing with this example, it may be useful to selectively activate 186 the cutting tip after a predetermined period without fluctuations in the received pressure signal. More generally, the received 182 signal may be processed as necessary to identify conditions in the volume suitable for selective activation 186 of the cutting tip.

In general, positioning 184 the cutting tip along the three-dimensional contour within the volume may be achieved according to any one or more of the various different techniques described herein for moving a cutting tip. For example, positioning 184 the cutting tip along the three-dimensional contour within the volume may include sending one or more control signals to an actuator directly or indirectly mechanically coupled to the cup and the cutting tip. In this context, the actuator should be understood to include any one or more of the various different mechanisms for moving the cutting tip. Thus, for example, the one or more control signals can move one or both of a pivot arm or an extension arm directly or indirectly (e.g., via cables) coupled to the cutting tip. More generally, the actuator can have a plurality of degrees of freedom, and sending the one or more control signals to actuator can include sending a respective control signal associated with each degree of freedom of the actuator. Thus, for example, in instances in which the actuator has six degrees of freedom, sending the one or more control signals to the actuator can include sending six control signals—one control signal for each degree of freedom—to the actuator. In certain implementations, the cutting tip can define a tip axis, and the one or more control signals sent to the actuator position the tip axis tangent to the three-dimensional contour, for example, as described above.

The three-dimensional contour can be any of the three-dimensional contours described herein. Thus, for example, the three-dimensional contour can be at least a portion of an ellipsoid or another shape formed through rotation of a curvilinear profile about an axis. Additionally, or alternatively, the three-dimensional contour may be substantially symmetric with respect to one or more planes bisecting the cup.

Selective activation 186 of the cutting tip can include, for example, delivering energy—such as, heat or other energy sufficient to dissect tissue—to the cutting tip based on the received 182 signal indicative of fluid pressure in the volume. While the selective activation 186 of the cutting tip can be based on the received 182 signal indicative of fluid pressure in the volume, it should be appreciated that selective activation 186 can further, or instead, be based on any one or more other signals described herein. Thus, for example, the selective activation 186 can be based on the received 182 signal indicative of fluid pressure in the volume in addition to confirmation, based on signals from one or more sensors on the cutting tip, that the cutting tip is appropriately positioned relative to the skin and tissue.

In certain implementations, selective activation 186 of the cutting tip can include delivering energy to the cutting tip based on whether the received 182 signal corresponds to a condition at or below a predetermined vacuum pressure in the volume. Given that sufficient vacuum pressure in the volume can draw skin of the patient toward the at least one surface of the cup, the received 182 signal indicative of a vacuum pressure in the volume can serve as a useful proxy for determining that skin along the breast is appropriately positioned relative to the at least one surface of the cup, and thus relative to three-dimensional contour, for carrying out the formation of a skin envelope according to any one or more of the techniques described herein. For example, the received 182 signal can form part of a control approach to maintain a target vacuum pressure in the volume defined by the at least one surface of the cup, thus maintaining proper positioning of the three-dimensional contour relative to skin of the breast. As a more specific example, the received 182 signal can be used as a feedback control parameter useful for controlling a vacuum source (e.g., a vacuum pump) in fluid communication with the volume. Further, or instead, other parameters may be useful as direct or indirect indications of appropriate positioning of skin along the breast relative to the at least one surface of the cup. For example, any manner and form of optical, thermal, electrical, and contact sensing may be used as an additional or alternative indication of positioning of skin of the breast relative to the at least one surface of the cup.

The exemplary method 180 can, in certain instances, include repeating 188 the steps of receiving 182 the signal, positioning 184 the cutting tip along the three-dimensional contour within the volume, and selectively 186 activating the cutting tip to dissect tissue to form a skin envelope. Once the three-dimensional skin envelope is formed, a physician may complete the mastectomy by removing tissue along the chest wall.

Figure 9:
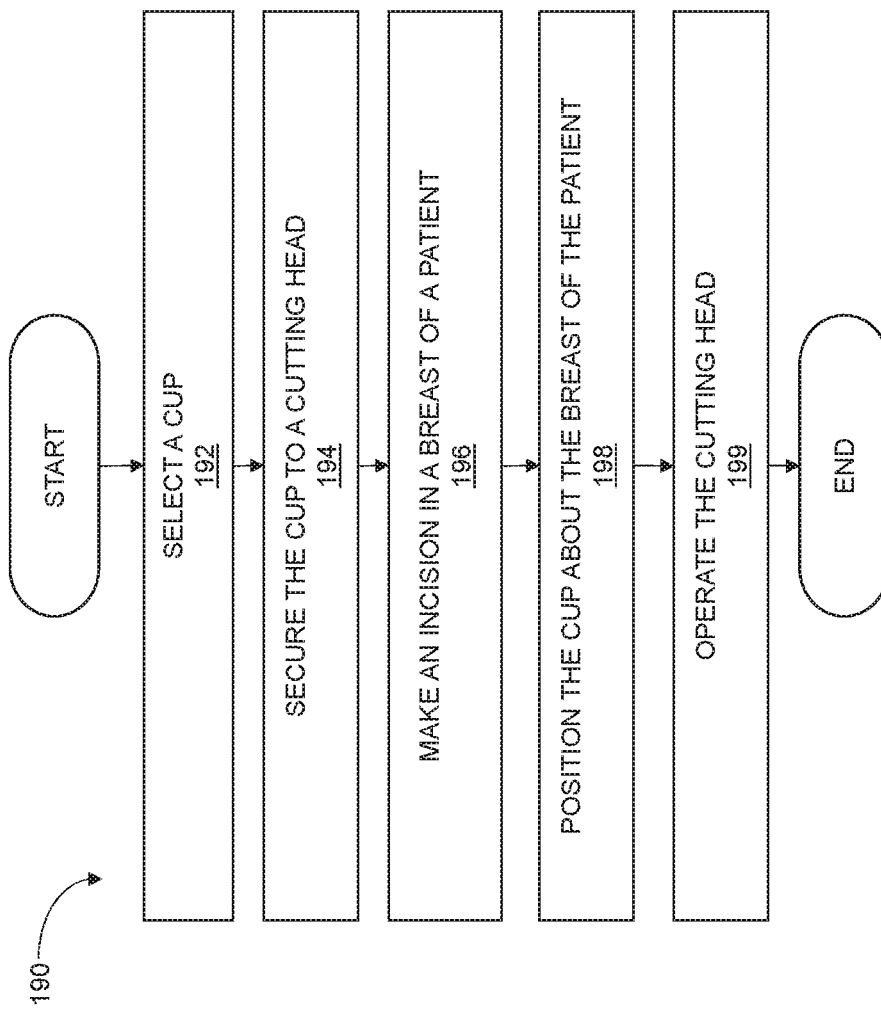
FIG. 9 is a flowchart of an exemplary method of removing breast tissue from a patient.
Figure 10:
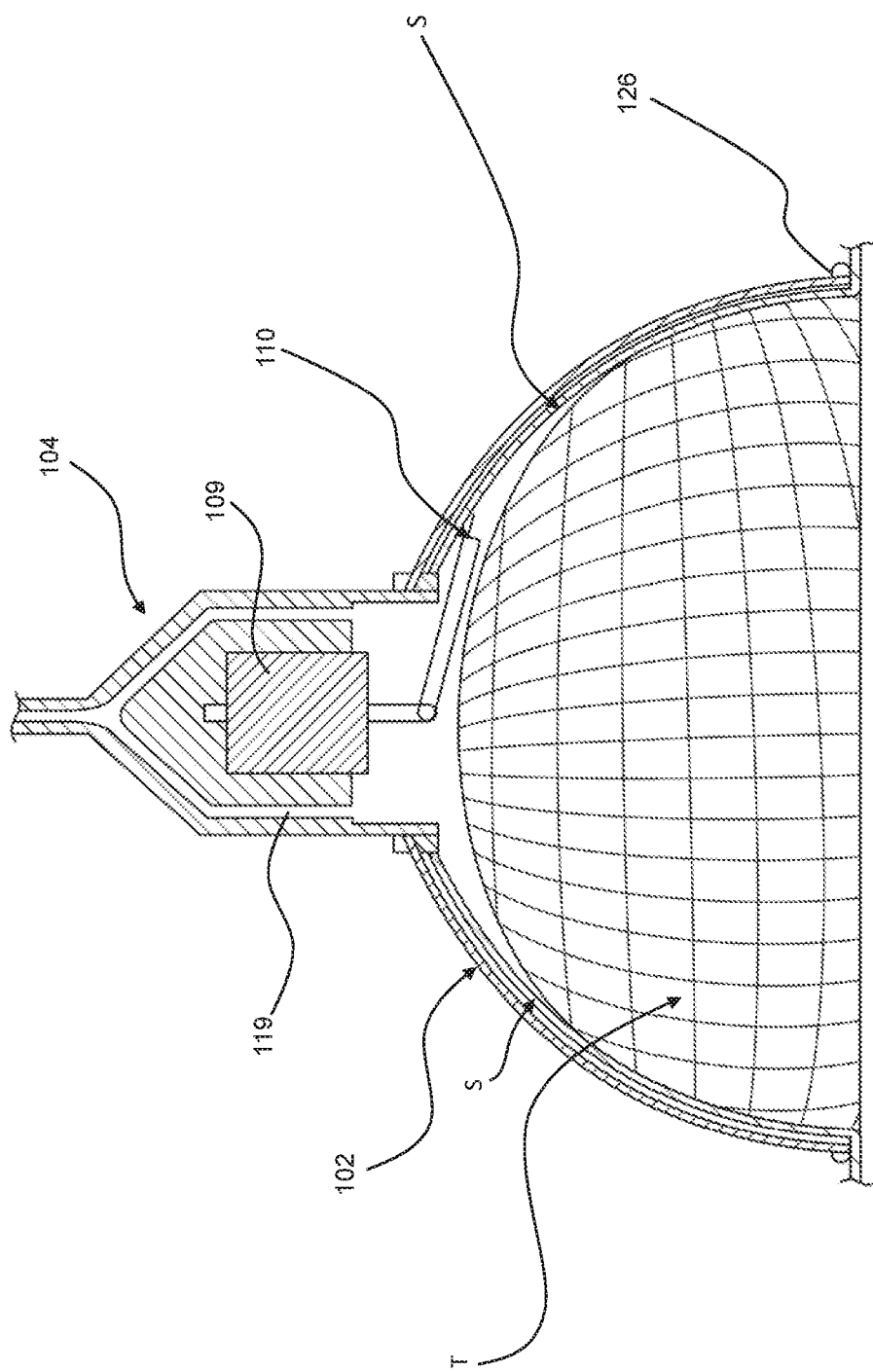
FIG. 10 is a schematic representation of the system of FIG. 1 positioned on a breast of a patient as a skin envelope is formed.

Referring now to FIGS. 9 and 10, an exemplary method 190 of removing breast tissue from a patient is described below in the context of a physician using the system 100 described in FIG. 1. However, unless otherwise specified or made clear from the context, it should be appreciated that the exemplary method 190 can be carried out by a physician operating on a patient using any one or more of the devices and systems described herein.

The exemplary method 190 can include selecting 192 a cup, securing 194 the cup to a cutting head, making 196 an incision in a breast of the patient, and positioning 198 the cup about the breast of the patient. It should be understood that the cup can be any one or more of the various different cups described herein and, thus, can be the cup 102. Further or instead, the cutting head can be any one or more of the various different cups described herein and, thus, can be the cutting head 104 including the actuator 109 and the cutting tip 110. For example, as shown in FIG. 10, the cutting tip 110 can be positioned adjacent to skin "S" of the breast and selectively activated to separate the skin "S" of the breast from tissue "T" of the breast to form a skin envelope. Suction applied via the suction lumen 119 defined by the cutting head 104 can draw the skin "S" toward the cup 102 as the tissue "T" falls away, with the resulting separation between the skin "S" and the tissue "T" providing more space for further maneuvering the cutting tip 110 to remove additional tissue. In this way, the cutting tip 110 can be progressively moved along the three-dimensional contour 111 (FIG. 4) and selectively activated to form the skin envelope.

Selecting 192 the cup can include selecting any one or more of the various different cups described herein, with the selected 192 cup having one or more surfaces defining a volume and a first opening. Selecting 192 the cup can include, among other things, choosing a cup approximating the size of the patient's breast. For example, the cup can be selected 192 from a plurality of cups spanning a range of sizes. More specifically, the plurality of cups can span variations in any one or more of base width, projection (distance from the chest wall when viewed from a side of the breast), size of the areola complex, or any other geometric feature of a breast. Further, or instead, selecting 192 the cup can include any manner and form of customization of the cup with respect to the patient's breast. Accordingly, in certain instances, selecting 192 the cup can include forming the cup in the specific shape of the patient's breast. In certain implementations, selecting 192 the cup can include providing a verification input to a user interface (e.g., a keyboard, a mouse, a touch screen, etc.) in electrical communication with the cutting head.

In general, securing 194 the cup to the cutting head can include at least mechanically coupling the cutting head to the selected 192 cup such that movement of the cutting head is at least partially restrained with respect to the cup as the procedure is carried out. In certain implementations, securing 194 the cup to the cutting head can further include establishing fluid communication between the cutting head and the volume defined by the cup such that suction provided through the cutting head can be provided in the volume to draw skin toward the at least one surface of the cup. Further, or instead, securing 194 the cup to the cutting head can, further or instead, include establishing electrical or other similar type of communication between the cup and a controller in electrical communication with the cutting head, with such communication being useful for identifying the cup. The electrical communication can include any one or more of the various different types of electrical communication described herein and generally useful for additionally or alternatively verifying the size of the cup or, in certain instances, for tracking the number of uses of the cup.

Making 196 an incision in the breast of the patient forms an access site for the cutting tip. In certain implementations, making 196 the incision can include removing the areola complex of the breast. For example, the physician can manually remove the areola complex from the breast according to any one or more conventional techniques.

Positioning 198 the cup about the breast of the patient can include placing one or more surfaces of the cup facing a skin surface of the breast with a first opening of the cup circumscribing the breast of the patient. In general, positioning 198 the cup about the breast of the patient can include positioning the cup about the breast of the patient according to any one or more of the techniques described herein. By way of example, therefore, positioning 198 the cup about the breast of the patient can include placing a gasket (e.g., the gasket 126) along a first opening defined by one or more surfaces of the cup. The gasket can be useful, for example, for creating a substantially sealed engagement with the chest wall when the cup is positioned over the breast. Continuing with this example, positioning 198 the cup about the breast of the patient can include forming at least a partial vacuum between the one or more surfaces of the cup and the skin surface of the breast to draw the breast toward the cup, as described above.

In certain implementations, positioning 198 the cup about the breast of the patient can include substantially centering the cup relative to the incision in the breast of the patient. Such substantial centering can be useful for increasing the likelihood that the cutting tip can extend sufficiently to reach each portion of the three-dimensional contour.

In certain implementations, the exemplary method 190 can further include operating 199 the cutting head. In general, operating 199 the cutting head can include controlling the cutting tip and the actuator according to any one or more of the various different methods described herein. Thus, the actuator can be actuated according to any one or more of the various different methods described herein to move the cutting tip along the three-dimensional contour at one or more predetermined distances from the one or more surfaces defining the volume and the first opening. Further, or instead, the delivery of energy to the cutting tip can be controlled to dissect tissue along the three-dimensional contour according to any one or more of the various different methods described herein.

While certain implementations have been described, other implementations are additionally or alternatively possible.

As yet another example, a transmitter for providing information about a cup to a controller has been described as including an RFID tag, it should be appreciated that other types of identification are additionally, or alternatively, possible. For example, referring again to FIGS. 1-3, it should be understood that the transmitter 124 on the cup 102 can further or instead include a portion of an electrical circuit. The portion of the electrical circuit can have one or more electrical properties indicative of the information related to the cup 102. In use, the portion of the electrical circuit carried on the cup 102 can be connectable to a receiver (e.g., a complementary portion of a pin and socket connector or other similar physical connection) carried on the cutting head 104 to complete an electrical circuit. The controller 106 can determine the size of the cup 102 based on the electrical properties of the completed electrical circuit. That is, a completed electrical circuit including a smaller size of the cup 102 can have different electrical characteristics than a completed electrical circuit including a larger size of the cup 102. As compared to the use of RFID to provide size information of the cup 102, transmitting size information from the cup to the controller through electrical properties of a hardwired electrical circuit can be useful for verifying size information of the cup without the use of a separate communication channel and, further or instead, can also provide a useful indication of a proper connection between the cup 102 and the cutting head 104.

In certain implementations, the portion of the electric circuit can have a predetermined impedance associated with size information of the cup 102. As an example, a larger size of the cup 102 can have a larger impedance than a smaller size of the cup 102. Continuing with this example, a detected impedance of the completed electrical circuit can provide an indication of the size of the cup 102. In certain instances, if the detected impedance does not correspond to one or more predetermined impedances, the controller 106 can provide an indication to the physician to check the connection and/or to check the condition of the cup 102. Further or instead, the controller 106 can lock activation of the cutting head 104 unless and until an impedance matching the one or more predetermined impedances is detected, indicating that the cup 102 is appropriately connected to the cutting head 104.

Further or instead, the transmitter 124 can include one or more pins associated with size information of the cup. For example, with the cup 102 connected to the cutting head 104, the position of the one or more pins of the transmitter 124 can identify the size of the cup 102. That is, detecting one or more pins associated with the cup 102 positioned in one or more corresponding receptacles of the cutting head 104 can be indicative of the size of the cup 102. As a more specific example, detecting a pin in a first position may be indicative of a first size of the cup 102, and detecting a pin in a second position may be indicative of a second size of the cup 102.

As another example, while the transmitter 124 has been described as providing information related to the size of the cup 102, it should be appreciated that the transmitter 124 can, further or instead, transmit other information, such as any manner and form of information useful for the safe and effective use of the cup 102. For example, the transmitter 124 may include a memory having stored thereon information related to the use history of the cup 102. As a more specific example, the use history of the cup 102 may be incremented according to each detected connection of the cup 102 as part of the system 100—such as a connection between the cup 102 and the cutting head 104, recognition of the cup 102 by the controller 106, or other similar proxies for use of the cup 102. Further or instead, the use history of the cup 102 may be incremented according to an input by the physician via the controller 106.

As still another example, while the transmitter 124 has been described as being in electrical communication (e.g., via RF communication and/or direct electrical connection) with the cutting head 104, it should be more generally understood that communication between the transmitter 124 and the cutting head 104 can include any manner and form of communication useful for transmitting information from the transmitter 124 (e.g., size and/or use history information) to the controller 106. Thus, for example, the transmitter 124 may be connectable in optical communication with a corresponding receiver carried on the cutting head 104 or other portion of the system 100. Continuing with this example, the transmitter 124 may include a QR code, a bar code, and/or other similar pattern associated with size of the cup 102. Further, or instead, the transmitter 124 may be activatable (e.g., via an interrogation signal including an optical signal) to transmit light of a predetermined wavelength associated with the size of the cup 102. That is, the size of the cup 102 may be determined based on a received wavelength (e.g., a detected color) associated with the cup 102.

As yet another example, while a suction channel has been described as extending through a cutting head, it should be appreciated that other configurations are additionally, or alternatively, possible. For example, one or more suction channels can be defined or at least partially defined by a cup positioned over a breast of a patient.

Figure 11B:
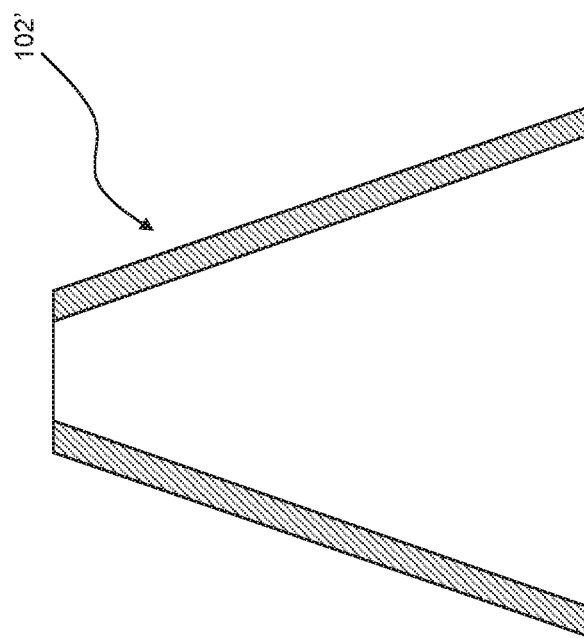
FIG. 11B is a cross-sectional view of the frustoconical cup of FIG. 11A along line B-B in FIG. 11A.
Figure 11A:
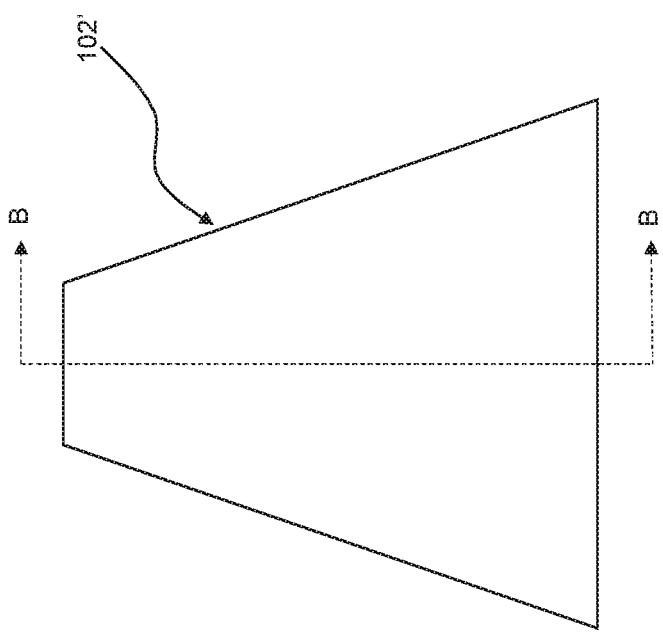
FIG. 11A is a side view of a frustoconical cup.

As still another example, while the volume defined by the at least one surface of the cup has been described as having certain shapes, other shapes are additionally or alternatively possible. For example, referring now to FIGS. 11A and 11B, a cup 102' can have at least one surface 112' defining a volume 114', and the at least one surface 112' of the cup 102' can be frustoconical. Unless otherwise specified or made clear from the context, it should be understood that the cup 102' can be used interchangeably with the cup 102 (FIG. 1). Further, for the sake of efficient description, elements with prime (') element numbers in FIGS. 10A and 10B should be understood to be similar to elements with unprimed elements numbers in FIGS. 1-4 and are not described separately, except to point out certain differences or emphasize certain aspects. Thus, for example, the cup 102' can be placed over a breast of a patient and, through the application of suction according to any one or more of the methods described herein, skin of the breast of the patient can be drawn toward the at least one surface 112'. As compared to other curved wall shapes, the frustoconical shape of the at least one surface 112' can be cost-effectively fabricated and, in some instances, can be fabricated with tighter dimensional tolerance. Further or instead, as compared to more complex curved wall shapes, the frustoconical shape of the at least one surface 112' can facilitate determination of a three-dimensional contour based on the at least one surface 112'.

Figure 12B:
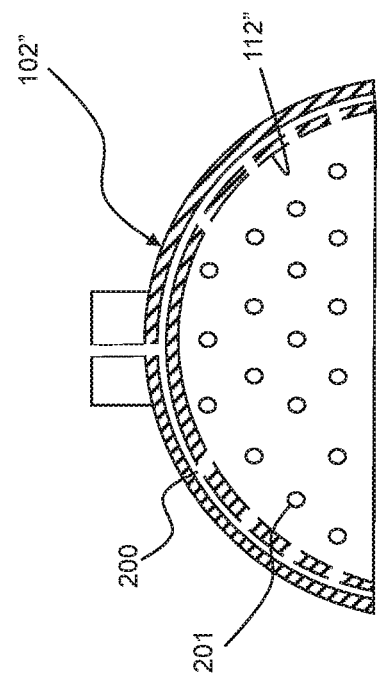
FIG. 12B is a cross-sectional view of the cup of FIG. 12A along line C-C in FIG. 12A.
Figure 12A:
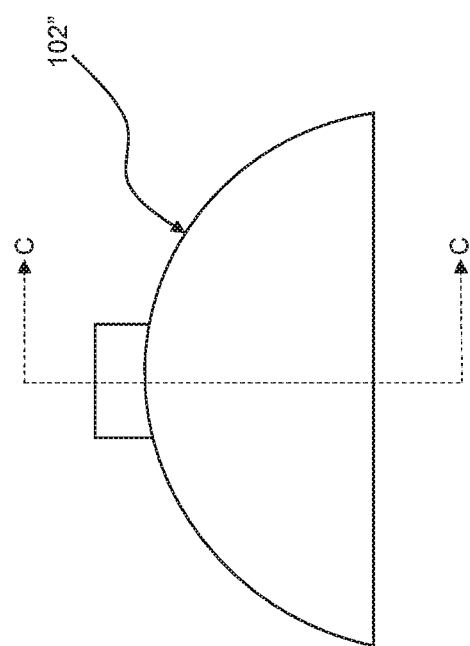
FIG. 12A is a side view of a cup defining suction channels.

As yet another example, while a suction channel has been described as extending through a cutting head securable to a cup, it should be appreciated that other configurations are additionally or alternatively possible for distributing suction along skin of the breast of the patient. For example, referring to FIGS. 12A and 12B, a cup 102" can define at least partially define one or more suction channels 200 and, optionally, at least one surface 112" a plurality of orifices 201 along the cup 102" such that suction is applied at multiple locations along the breast of the patient. Unless otherwise specified or made clear from the context, it should be understood that the cup 102' can be used interchangeably with the cup 102 (FIG. 1) and the cup 102' (FIGS. 10A and 10B). Further, for the sake of efficient description, elements with double prime (") element numbers in FIGS. 12A and 12B should be understood to be similar to elements with unprimed elements numbers in FIGS. 1-4 and primed element numbers in FIGS. 11A and 11B and are not described separately, except to point out certain differences or emphasis certain aspects. Thus, for example, the cup 102" can be placed over a breast of a patient and, through the application of suction according to any one or more of the methods described herein, skin of the breast of the patient can be drawn toward The arrangement of the plurality of orifices 201 along the cup 102" may be in any one or more of various different patterns useful for distributing vacuum suction along skin of the breast of the patient. That is, the pattern of the plurality of orifices 201 may be particularly useful for drawing skin of the breast of the patient toward the at least one surface 112" to form a three-dimensional contour useful for carrying out any one or more of the various different methods described herein. Further, or instead, distribution of the vacuum suction along the plurality of orifices 201 may be useful for holding the cup 102" in place during a procedure.

Figure 2:
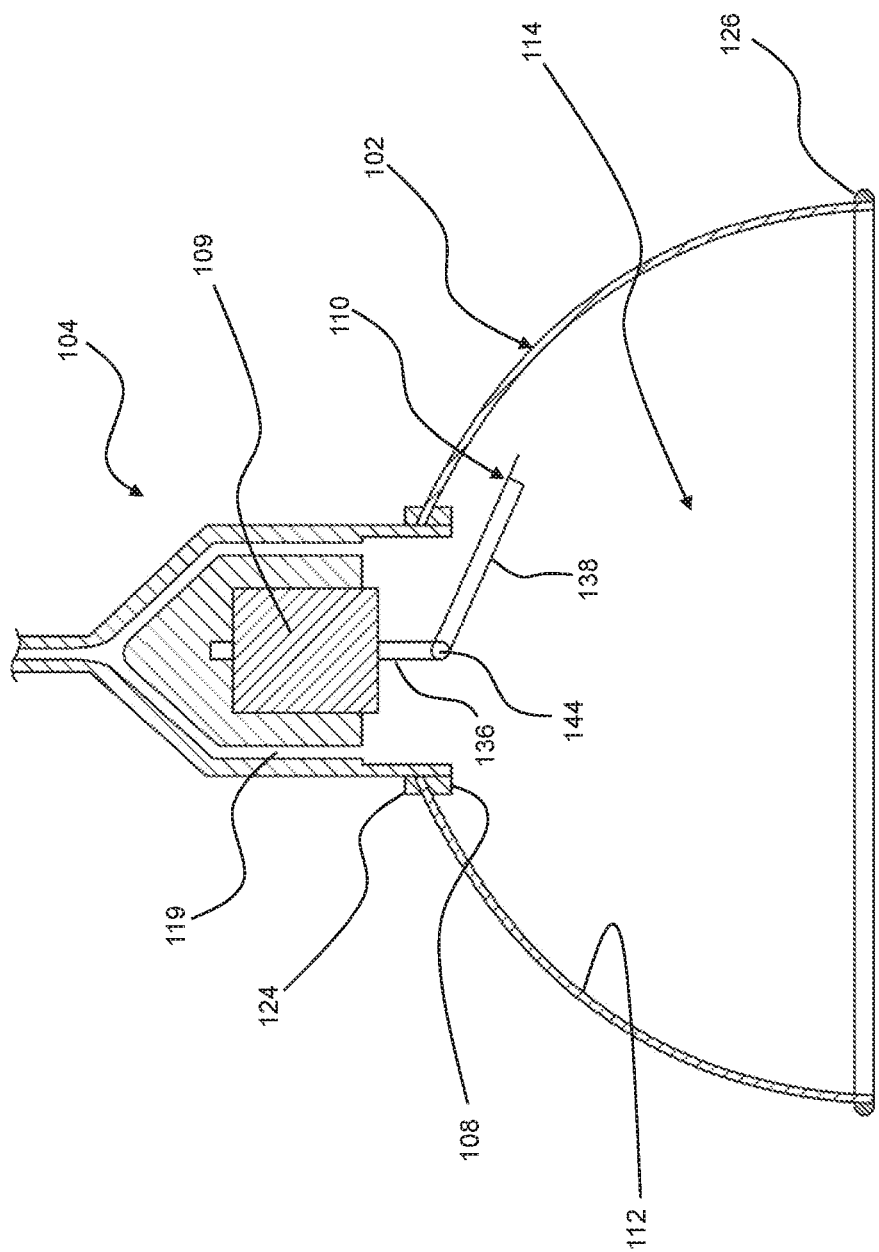
FIG. 2 is a side view of cross-section of a cutting head and a cup of the system of FIG. 1, the cross-section taken along line A-A in FIG. 1.
Figure 3:
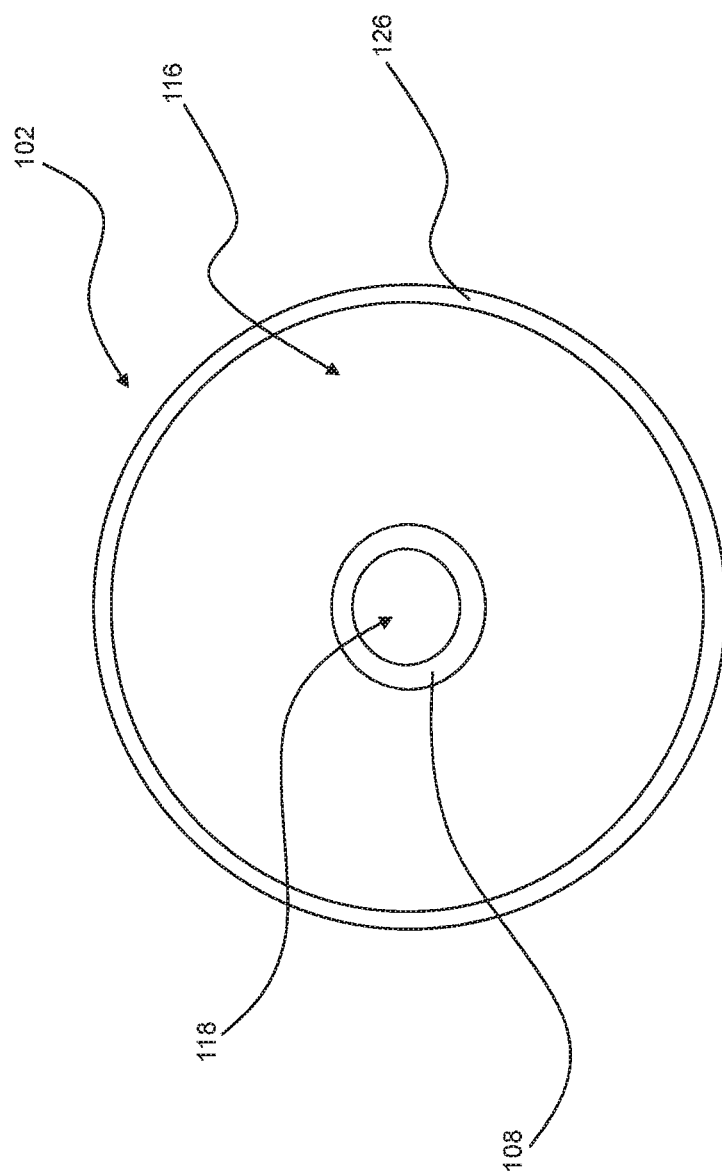
FIG. 3 is a bottom view of the cup of the system of FIG. 1.
Figure 4:
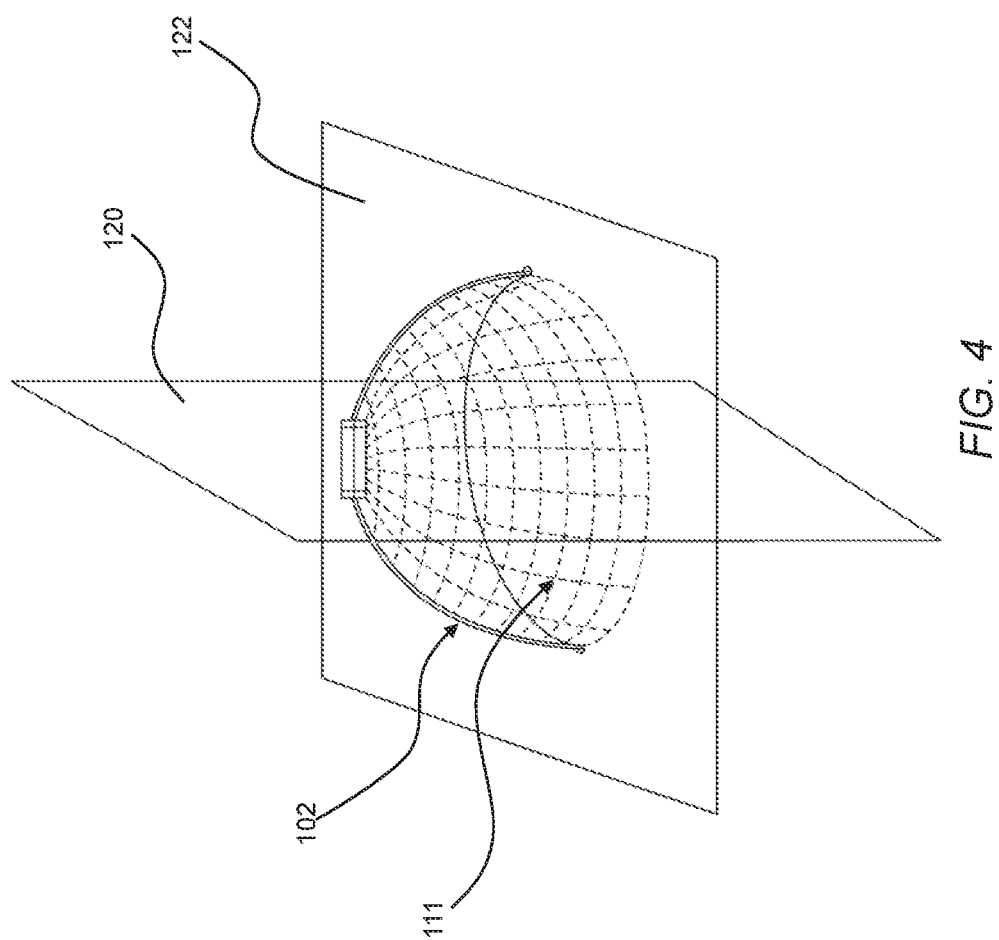
FIG. 4 is a schematic representation of a three-dimensional contour within a volume of the cup of the system of FIG. 1.
Figure 5:
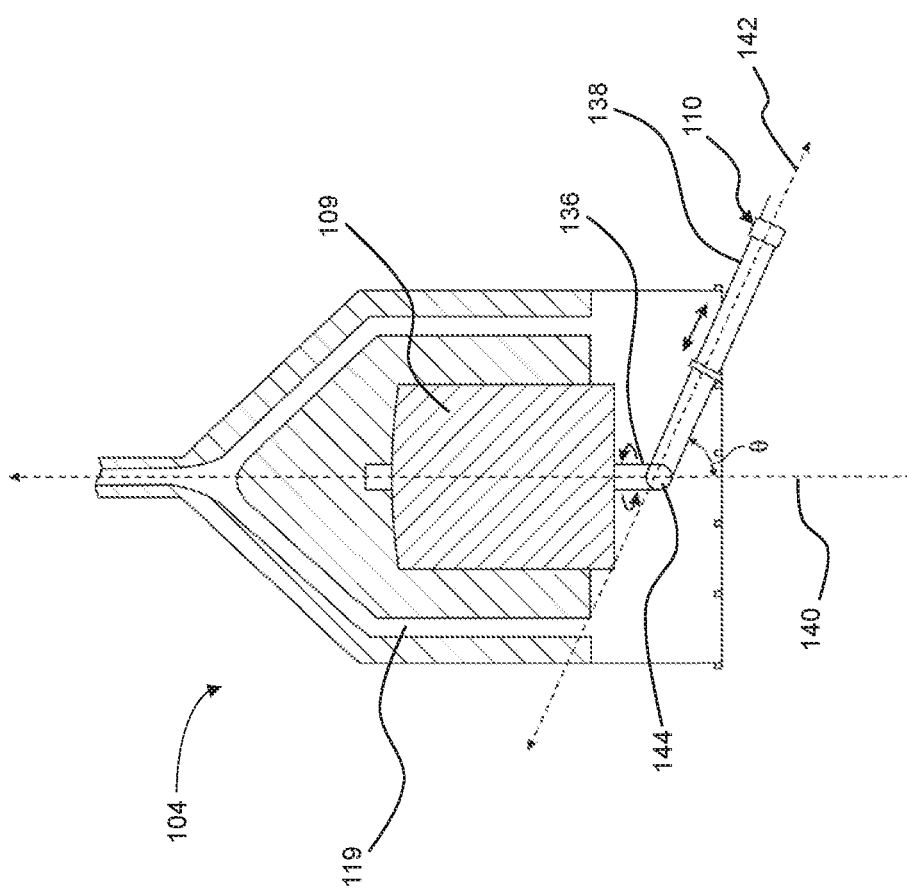
FIG. 5 is a side view of a cross-section of the cutting head of the system of FIG. 1, the cross-section taken along line A-A in FIG. 1.
Figure 6:
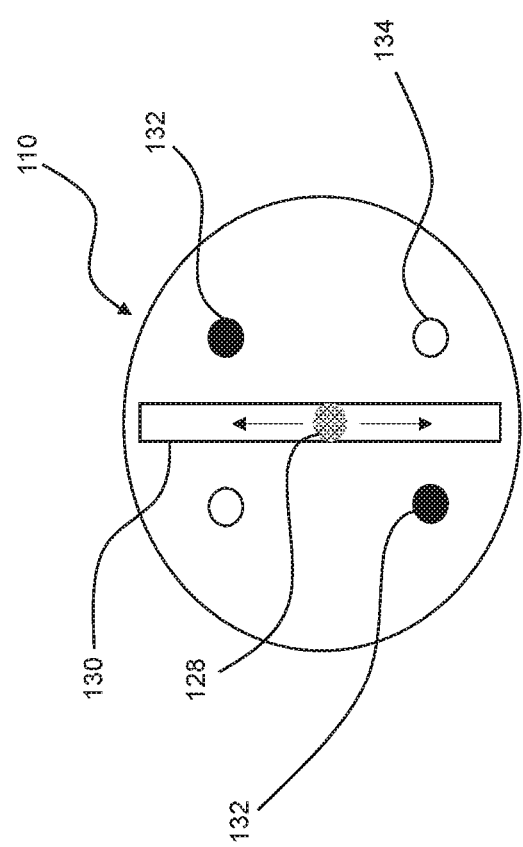
FIG. 6 is an end view of a cutting tip of the cutting head of the system of FIG. 1.
Figure 13:
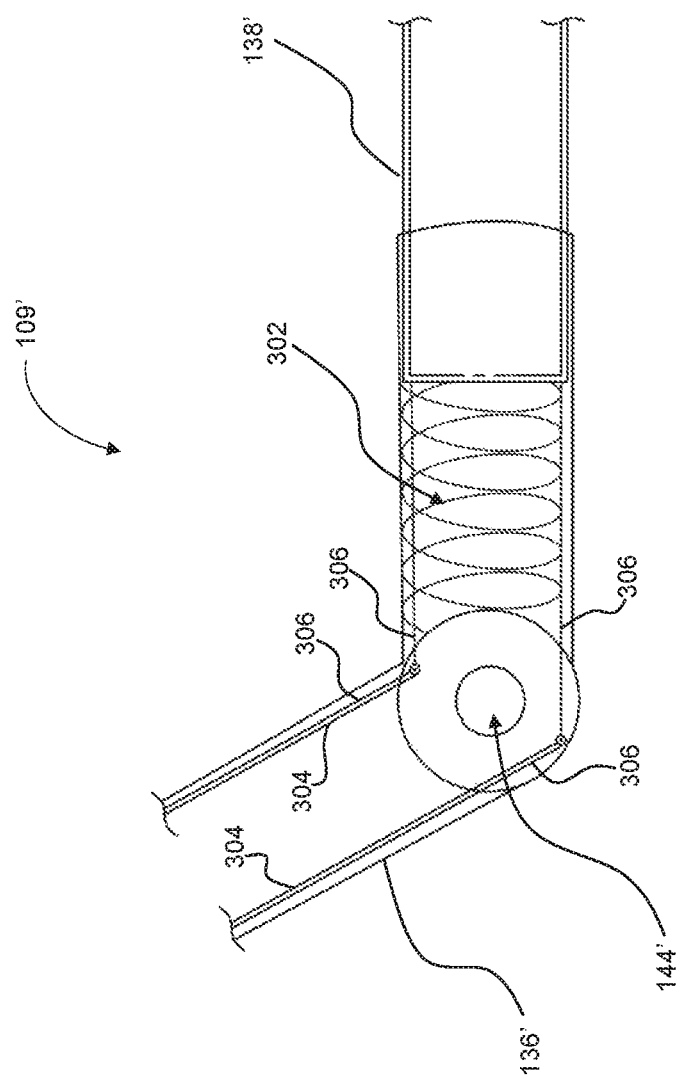
FIG. 13 is a cross-sectional view of a portion of an actuator of a cutting head including a spring and cables.

As still another example, while movement of an extension arm has been described as being achieved through the use of a linear actuator and an electric rotary actuator, other types of actuation can additionally or alternatively be used to move the extension arm as required for positioning a cutting tip along a three-dimensional contour. For example, referring now to FIG. 13, an actuator 109' useable with a cutting head (e.g., cutting head 104 in FIG. 2) can include a pivot arm 136', an extension arm 138', a pivot joint 144', a spring 302, pivot cables 304, and extension cables 306. Further, for the sake of efficient description, elements with primed numbers (') in FIG. 13 should be understood to be similar to elements with unprimed element numbers in FIG. 2 and are not described separately, except to point out differences. Thus, for example, the extension arm 138' can be coupled to a cutting tip such as the cutting tip 110 (FIG. 2).

A cutting tip attached to the actuator 109' can be positioned through actuation of the spring 302, the pivot cables 304, the extension cables 306, or combinations thereof to move the pivot arm 136' and the extension arm 138'. For example, the spring 302 can be positioned to bias movement of the extension arm 138' to move a cutting tip away from the pivot joint 144'. Further, or instead, tension in the extension cables 306 can be controlled to control movement of a cutting tip away from the pivot joint 144'. That is, as tension in the extension cables 306 is greater than the force of the spring 302, the extension cables 306 can shorten the length of the extension arm 138' to move a cutting tip toward the pivot joint 144'. Continuing with this example, it should be further appreciated that, as tension in the extension cables 306 equals the force of the spring 302, the position of the extension arm 138' can be fixed. Similarly, as tension in the extension cables 306 is less than the force of the spring 302, the spring 302, the bias of the spring 302 can move the extension arm 138' away from the pivot joint 144'. Additionally, or alternatively, differences in tension between the pivot cables 304 can change an angle of the extension arm 138' relative to the pivot arm 136'.

The above systems, devices, methods, processes, and the like may be realized in hardware, software, or any combination of these suitable for a particular application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. In another aspect, the methods may be embodied in systems that perform the steps thereof, and may be distributed across devices in a number of ways. At the same time, processing may be distributed across devices such as the various systems described above, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all of the steps thereof. The code may be stored in a non-transitory fashion in a computer memory, which may be a memory from which the program executes (such as random access memory associated with a processor), or a storage device such as a disk drive, flash memory or any other optical, electromagnetic, magnetic, infrared or other device or combination of devices. In another aspect, any of the systems and methods described above may be embodied in any suitable transmission or propagation medium carrying computer-executable code and/or any inputs or outputs from same.

The method steps of the implementations described herein are intended to include any suitable method of causing such method steps to be performed, consistent with the patentability of the following claims, unless a different meaning is expressly provided or otherwise clear from the context. So, for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It will be appreciated that the methods and systems described above are set forth by way of example and not of limitation. Numerous variations, additions, omissions, and other modifications will be apparent to one of ordinary skill in the art. Absent an explicit indication to the contrary, the disclosed steps may be modified, supplemented, omitted, and/or re-ordered without departing from the scope of this disclosure. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed is:

1. A method of controlling three-dimensional dissection of tissue, the method comprising:
   receiving an identification signal indicative of size of a cup, the cup having at least one surface, the at least one surface defining a volume and a first opening;
   based on the identification signal, determining a three-dimensional contour within the volume, the three-dimensional contour spaced apart from the at least one surface at one or more predetermined distances;
   sending one or more control signals to an actuator coupled to a cutting tip, the actuator coupled to the cup and extending into the volume defined by the at least one surface of the cup, the one or more control signals associated with positioning the cutting tip along the three-dimensional contour; and
   sending an activation signal to the cutting tip to dissect tissue along the three-dimensional contour to form at least a portion of a skin envelope.

2. The method of claim 1, wherein receiving the identification signal includes sending an interrogation signal to the cup.

3. The method of claim 1, wherein the identification signal is further indicative of use history of the cup, and sending the one or more control signals to the actuator is based on whether the use history of the cup is below a predetermined threshold.

4. The method of claim 1, wherein the three-dimensional contour is parallel to and spaced apart from the at least one surface of the cup.

5. The method of claim 1, wherein determining the three-dimensional contour within the volume includes receiving, from an input device, the one or more predetermined distances.

6. The method of claim 1, wherein determining the three-dimensional contour within the volume includes detecting one or more electrical properties of the identification signal, the one or more electrical properties associated with a size of the cup.

7. The method of claim 1, wherein the cutting tip defines a tip axis, and the one or more control signals position the tip axis tangent to the three-dimensional contour.

8. The method of claim 1, further comprising sending an alert signal to a user interface, the alert signal based on proximity of the cutting tip to a predetermined region of the volume.

* * * * *